United States Patent
Kloecker et al.

(10) Patent No.: US 8,052,630 B2
(45) Date of Patent: Nov. 8, 2011

(54) SEGMENTED PNEUMATIC PAD REGULATING PRESSURE UPON PARTS OF THE BODY DURING USAGE

(75) Inventors: Richard J. Kloecker, St. Louis, MO (US); Kent F. Schien, Chesterfield, MO (US); James A. Muir, Ballwin, MO (US); Richard P. Lux, St. Louis, MO (US)

(73) Assignee: Innovative Medical Corporation, Chesterfield, MO (US)

( * ) Notice: Subject to any disclaimer, the term of this patent is extended or adjusted under 35 U.S.C. 154(b) by 292 days.

(21) Appl. No.: 12/454,783

(22) Filed: May 23, 2009

(65) Prior Publication Data
US 2010/0042026 A1     Feb. 18, 2010

Related U.S. Application Data

(63) Continuation-in-part of application No. 11/051,606, filed on Feb. 4, 2005, now abandoned, which is a continuation-in-part of application No. 10/208,164, filed on Jul. 29, 2002, now Pat. No. 6,852,089, which is a continuation-in-part of application No. 10/008,545, filed on Nov. 13, 2001, now Pat. No. 6,436,064, which is a continuation-in-part of application No. 09/559,682, filed on Apr. 27, 2000, now Pat. No. 6,315,745.

(60) Provisional application No. 60/131,697, filed on Apr. 30, 1999.

(51) Int. Cl.
*A61L 15/00* (2006.01)

(52) U.S. Cl. .............. 602/75; 602/13; 602/63; 602/901; 601/151; 601/152; 128/878

(58) Field of Classification Search ................. 128/869, 128/876, 878, 882; 601/150–152, 134; 602/13, 602/61–63, 67, 23, 75–77, 901; 600/498; 374/4; 5/621, 654, 655.3, 707, 710, 713
See application file for complete search history.

(56) References Cited

U.S. PATENT DOCUMENTS

| | | |
|---|---|---|
| 3,888,242 A | 6/1975 | Harris et al. |
| 4,029,087 A | 6/1977 | Dye et al. |
| 4,091,804 A | 5/1978 | Hasty |
| 4,150,442 A | 4/1979 | Boone |
| 4,186,738 A | 2/1980 | Schleicher et al. |
| 4,207,876 A | 6/1980 | Annis |
| 4,256,094 A | 3/1981 | Kapp et al. |
| 4,269,175 A | 5/1981 | Dillon |
| 4,369,588 A | 1/1983 | Berguer |
| 4,374,518 A | 2/1983 | Villanueva |
| 4,396,010 A | 8/1983 | Arkans |
| 4,408,599 A | 10/1983 | Mummert |
| 4,657,003 A | 4/1987 | Wirtz |

(Continued)

*Primary Examiner* — Patricia Bianco
*Assistant Examiner* — Tarla Patel
(74) *Attorney, Agent, or Firm* — Paul M. Denk

(57) ABSTRACT

A compression garment or pad for selective application for treatment of lymphedema evidenced at various locations of the body. The pad includes a pair or series of layers of hermetically sealed material, that can capture pressurized air, when applied therein, and is formed through the patterned sealing of the layers of the pad together, at select locations, to form air pockets that can selectively apply isolated points of pressure to the patient's affected area, without disrupting normal vascular and lymphatic functioning. The pad is design cut, for either use in that matter, or for application as a garment to various segments of the body and can apply pressure over the entire affected area. The pad includes valves that allows for injection of measurable air, to the desired pressure points, or its deflation, after treatment.

21 Claims, 14 Drawing Sheets

U.S. PATENT DOCUMENTS

| | | |
|---|---|---|
| 4,744,391 A | 5/1988 | Lardner |
| 4,998,582 A | 3/1991 | Fudono et al. |
| 5,125,400 A | 6/1992 | Johnson, Jr. |
| 5,179,941 A | 1/1993 | Siemssen et al. |
| RE34,661 E | 7/1994 | Grim |
| 5,328,445 A | 7/1994 | Spahn et al. |
| 5,437,610 A | 8/1995 | Cariapa et al. |
| 5,443,440 A | 8/1995 | Tumey et al. |
| 5,450,858 A | 9/1995 | Zablotsky et al. |
| 5,487,197 A | 1/1996 | Iskra et al. |
| 5,575,762 A | 11/1996 | Peeler et al. |
| 5,591,200 A | 1/1997 | Cone et al. |
| 5,626,556 A | 5/1997 | Tobler et al. |
| 5,901,393 A | 5/1999 | Pepe et al. |
| 5,916,183 A | 6/1999 | Reid |
| 6,053,883 A | 4/2000 | Schiek |
| 6,154,907 A | 12/2000 | Cinquin |
| 6,315,745 B1 | 11/2001 | Kloecker |
| 6,436,064 B1 | 8/2002 | Kloecker |
| 6,478,757 B1 | 11/2002 | Barak |
| 6,494,852 B1 | 12/2002 | Barak et al. |
| 6,671,911 B1 | 1/2004 | Hill et al. |
| 6,689,074 B2 | 2/2004 | Seto et al. |
| 6,711,771 B2 | 3/2004 | Cook et al. |
| 6,823,549 B1 | 11/2004 | Hampton et al. |
| 6,852,089 B2 | 2/2005 | Kloecker et al. |
| 7,063,676 B2 | 6/2006 | Barak et al. |
| 7,278,179 B2 | 10/2007 | Schneider |

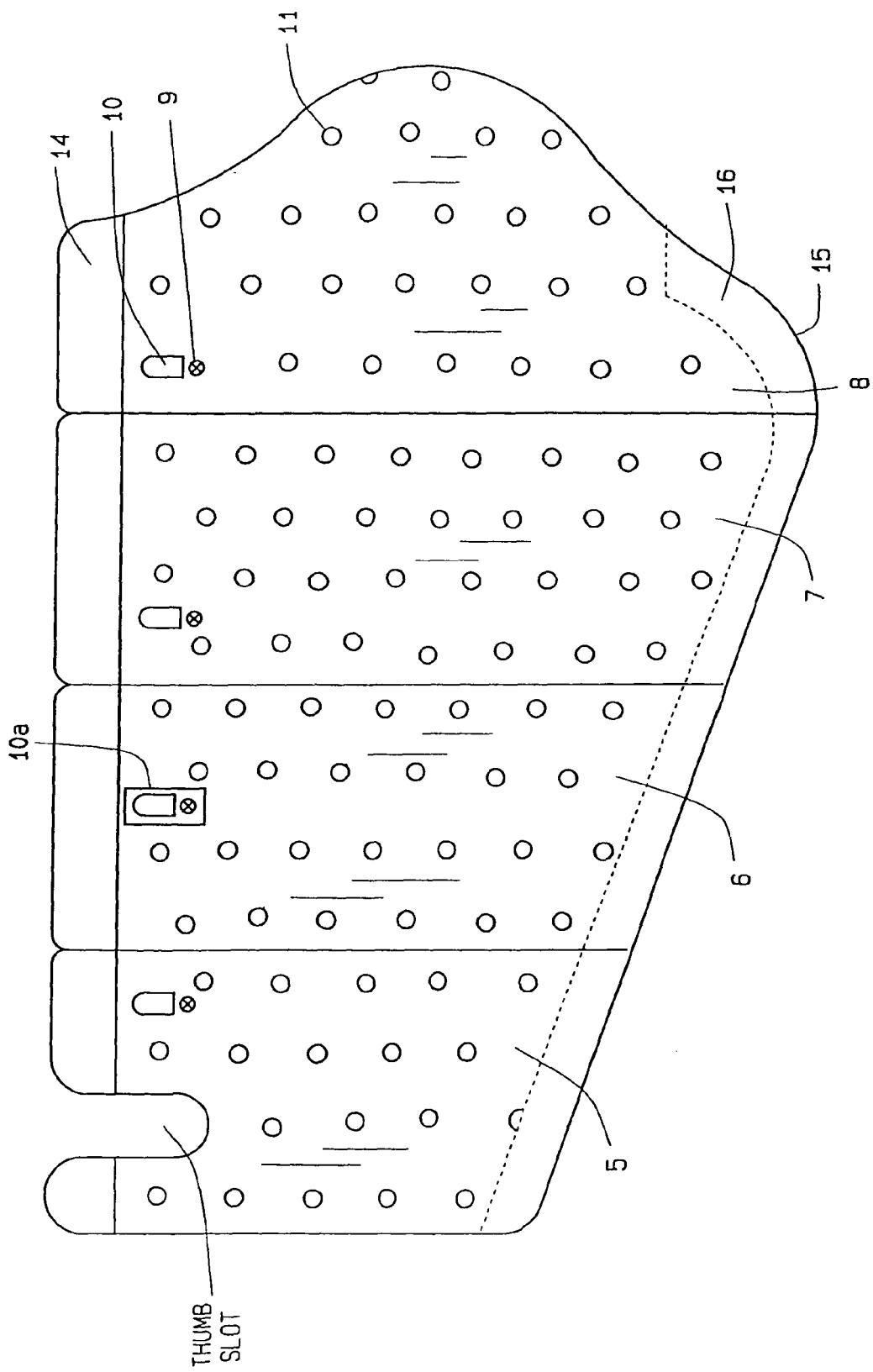

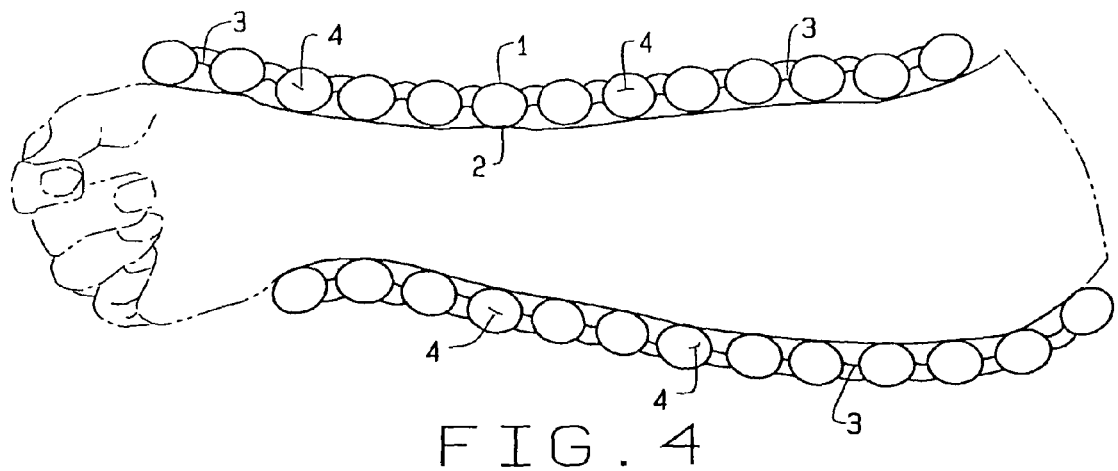
FIG. 4
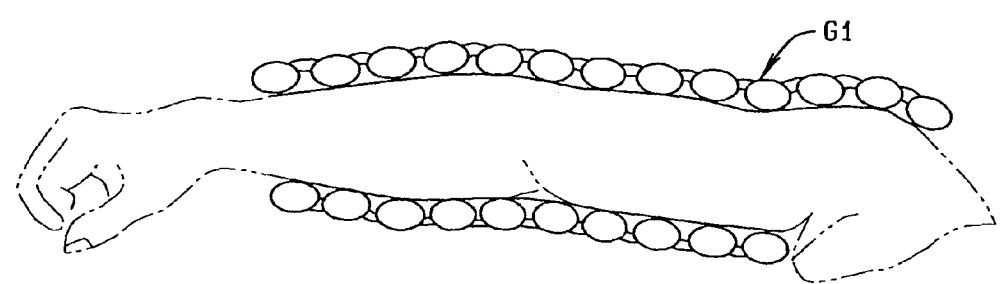
FIG. 5
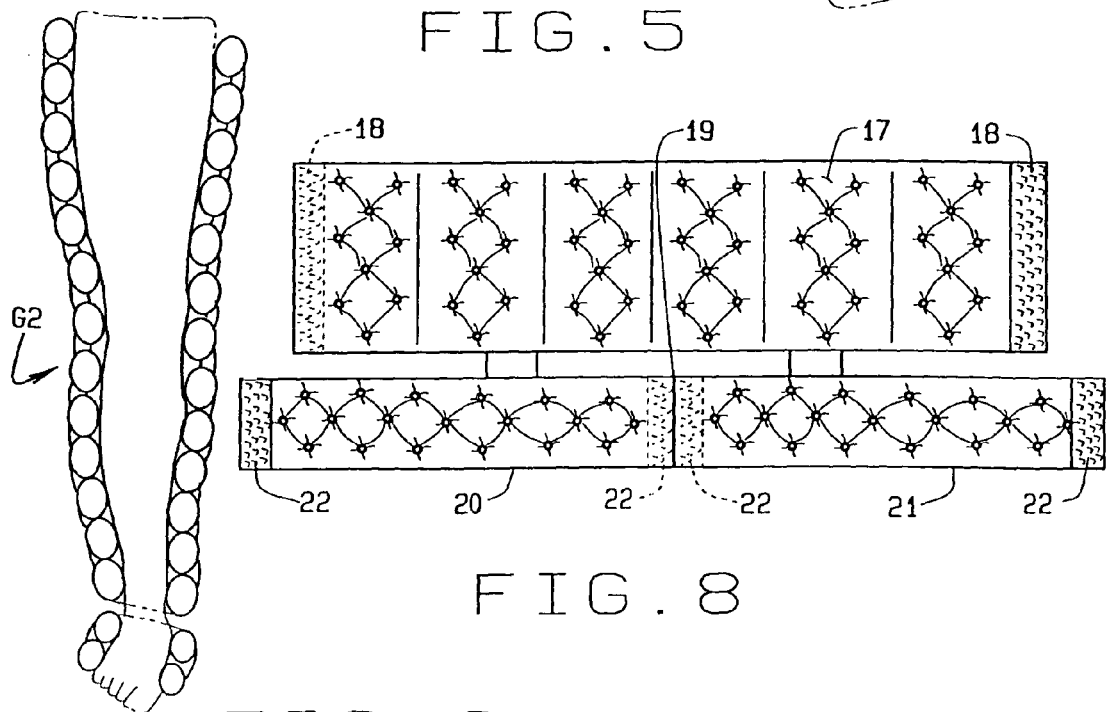
FIG. 6
FIG. 8

SEGMENTED PNEUMATIC PAD REGULATING PRESSURE UPON PARTS OF THE BODY DURING USAGE

CROSS REFERENCE TO RELATED APPLICATION

This continuation-in-part patent application claims priority to the U.S. application Ser. No. 11/051,606, filed on Feb. 4, 2005 now abandonded, which claims priority to continuation-in-part patent application Ser. No. 10/208,164, filed on Jul. 29, 2002 now U.S. Pat. No. 6,852,089, which is a continuation-in-part of the U.S. patent application Ser. No. 10/008,545, filed on Nov. 13, 2001, now having U.S. Pat. No. 6,436,064, issued on Aug. 20, 2002, which is a continuation-in-part of the U.S. patent application Ser. No. 09/559,682, filed on Apr. 27, 2000, now having U.S. Pat. No. 6,315,745, issued on Nov. 13, 2001; said previous application being related to its provisional application Ser. No. 60/131,697, filed on Apr. 30, 1999, all of said applications being owned by the same inventors.

BACKGROUND OF THE INVENTION

This invention relates primarily to the treatment of lymphedema, and the use of various instrumentation that can effectively lessen the painful and deleterious aspects of such disease as manifested in the body.

The occurrence of pressure of pressure ulcers has recently gained prominence as national health care issues. Such ulcers remain a major cause of morbidity and mortality. The National Pressure Ulcer Advisory Panel (NPUAP) defines a pressure ulcer as a area of unrelieved pressure over a defined area, usually a boney prominence, resulting in Ischemia, cell death, and tissue neurosis. The major sites for such ulcers include the ischium (28%), sacrum (17-27%), the femoral trcanter (12-19%), and the (9-18%). The incidence in hospitalized patients ranges from 3.5% to 69% depending on the risk factors and acute and chronic institutions. Surprisingly, the incidence is hirer in acute care institutions than in chronic long term care facilities. Operations for non elective orthopedic procedures, e.g. hip replacement and long bone fractures, have an incidence of 66% for those procedures. Increased time on the operating table also increases the risk of ulcers, with one study reporting an increased risk of 33% for every minute on the operating table for over four hours. In the nursing home environment, the prevalence of such ulcers ranges between 2.6-24%. In acute care facilities, it is 25%.

Pressure ulcers are one of the most costly diseases to treat. A study for vendors of medicare and Medicaid services, a conducted, and as reported, says that over 257,000 cases of preventable pressure ulcers occurred in the fiscal year of 2007. They also reported the average cost for treatment of one of these cases is over $43,000. That's over 11 billion dollars in preventable health care cost. Just recently, medicare has changed the payout rules at it will no longer pay for hospitable mistakes, one of which is hospital acquired pressure ulcers.

The accepted theorem for causing pressure ulcers is a sustained pressure on a surface of subcutaneous tissue, the pressure being in a range of 32 to 40 mn of hg for two hours. This is sufficient to close the capillary bed blood flow. A recent study demonstrated that pockets of subcutaneous edema when a person was in a prone position on a hard surface for one hour. An area subject to prolong pressure by a person lying on a hard surface, such as an operating table, applies pressure to the skin and subcutaneous tissues and place on the skin covering the coccyx tail bone for one hour. Post pressure was sonigraphically tested and images exhibited pockets of deep edema or lakes. These lakes of edema fluid (extra cellular fluid) caused a decrease of blood flow, both arterial and venous, and has contributed to the pathogenic development of pressure ulcers. Considering these findings of lakes of sub dermal extra cellular fluid as possible causes of pressure ulcers, it was a given conclusion that the principles of clearing lymphedema fluid would apply in the parts of the body affected by such pressure.

An earlier patent by one of the inventors herein, U.S. Pat. No. 6,315,745, defined a system of cycling air filled cellules arranged in a horizontal plain and controlled by a computerized pump could intermittently control the physiologic metabolism in a dynamic fashion and thus prevent the formation of these subcutaneous lakes form forming.

As is well known in the art, lymphedema is a collection of fluids within the tissue, usually extremities, such as one or both of the arms, one or both of the legs, and which is caused from various etiological causes. Lymphedema can be a primary illness that is congenital. This can either result from aphasia of the lymphatic system, which may occur as a result of a complete lack of development of the same, or can be caused by hyperplasia of the lymphatic, such as an underdevelopment of the lymphatic system. Furthermore, lymphedema can be caused, and result from inflammatory diseases. These include mostly bacteriological infections. The noninfectious inflammatory causes are due to a variety of impairments, such as malignancies where the lymphatics can be blocked by tumor cells, or the lymph nodes can be blocked by tumor cells. In addition, it can result from the surgical removal of various lymph nodes, and the surgical interruption of the normal performance of the lymphatics.

Furthermore, such can come from radiation that causes sclerosis or scarring of the lymphatics. Furthermore, such can result from chronic venous diseases of long standing origin. In addition, lymphedema can come from severe local injury to a limb. Furthermore, it is usually the infectious element that accompanies such an injury that may result in the onset of lymphedema. Lymphedema can also originate from the blockage of lymphatics by various parasites. Finally, pathology in lymphatics can come from various systemic diseases including myxedema, renal disease, such as nephritis or nephrosis, with loss of protein materials, and can derive from various collagen diseases and fibrotic diseases. All of these diseases result in obstruction of the lymphatic flow and thus causes an accumulation of fluids in the effected limb or limbs. It is also known that cardiac failure can also cause the onset of this malady.

Until recent years, the lymphatic system's anatomy has only been demonstrated in its larger or more gross form. Millions of small lymphatic ducts have not been truly understood or demonstrated until the past several years, and only as a result of extensive research. The smaller lymphatics, which were cannulated under the magnification of the electron microscope, have been demonstrated as playing a role in the onset of this type of disease. Such had been predicted for a number of years, but it was not demonstrated until approximately two years ago. Now, the network of the lymphatic system is fairly well understood and known. The lymph system is actually inherent in all of the bodily organs, but the major part of the lymphatic system in the extremities is in the subcutaneous tissues. Such has been demonstrated.

The effects of lymphedema on the patient are well known. Patients generally are somewhat or significantly disabled according to the limb that is affected. Usually, with the onset of lymphedema, the patient either has one or two lower limbs that are very heavily affected, and manifest a heavy accumulation of such body fluids. As the disease progresses, it hampers the patient's ambulation and makes it very difficult for normal clothing to fit. Eventually, normal everyday activities become limited.

If lymphedema effects the upper extremity, the hand is markedly affected, and the mobility of the hand, fingers and thumb, etc., are eventually also affected. In addition, these people, subject to lymphedema, are very susceptible to various other serious infections. A very slight portal of entry, such as a cut, pin stick, hangnail, or the like, or anything that allows the entrance of bacteria into the lymphatic system becomes a very serious cellulitic process. This can reach proportions of fever and chills, and even require hospitalization, and if uncontrolled can even cause septic shock and death. The reason for this is that the lymph fluid is a perfect media for bacteria to grow in and there is an abundance of such fluid in those subcutaneous tissues.

Lymphedema is commonly seen in either the upper or lower extremities of the body as mentioned above. This can be either individually, or isolated in its location, depending upon where the lymph nodes have been removed, or it can manifest itself in a variety of these extremities, after its onset. Some of the cases of lymphedema are normally due to chronic venous disease. However, the largest number of such cases have been caused by secondary reactions to radiation and radical surgery where either all of the lymph nodes were removed from a groin area, the pelvis, or from an axilla. There was no real algorithm of treatment until the late 1980's.

Currently, literature has become more proliferative on the problems associated with lymphedema. Studies, even by the inventor herein, have focused more attention to lymphedema, and have led to an extrapolation of some hypothesis as to its etiology at the level of the microscopic lymphatics.

There are a variety of treatments that are currently available for lymphedema, and most of them, relate to some type of wrapping or compression of the effected area, in an effort to reduce the accumulation of the fluids. Many of the processes have included various types of wraps, or pumps, for achieving a dissemination of the localized fluids.

For example, the Reid sleeve is one such instrument that has been used for the treatment of lymphedema. See U.S. Pat. No. 5,916,183. It is a sleeve type compression device, almost in the nature of a cast, but in this instance, formed of more flexible type of nylon or related materials. Then, a series of straps can be tightened around the sleeve, at the situs of the accumulated fluids, and tightened by means of any type of fastener associated with such straps, in order to apply compression at the site of treatment. Thus, the essence of the Reid sleeve is simply to provide a massive amount of physical pressure by tightening of a sleeve about the infected area.

The use of such compression bandaging has provided some beneficial results to the patient, and has achieved limb reduction, enhanced skin tone, and softer skin texture, but, the use of such a bandage does have the potentially harmful effects of functioning like a tourniquet upon the effected area, and unless the amount of pressure applied is significantly controlled, can have further detrimental effects in the nature of reducing blood circulation and flowage, which can be very harmful to the patient, if not properly supervised. Most of these sleeve type of devices, available in the art, may be initially applied by the medical practitioner, in the office, but once the patient takes it home, he/she will either be advised or have a tendency to apply such sleeves themselves, which can afford no regulation over the amount of pressure applied by such a compression sleeve, once installed.

It has also been suggested, recently, that some type of air compressive means or strap may extend, at a slight width, along the internal length of the Reid or related sleeves, and be pumped up to provide additional tightness to the device encompassing the limb. But, once again, such applications offer little or no control over the amount of pressure applied, or the benefits or harm that may result from their usage, particularly when applied by the patient alone.

Various United States patents have previously issued relating to technology available for treatment of accumulation of body fluids, or for other treatments. For example, in the U.S. Pat. No. 4,029,087, entitled "Extremity Compression Device," there is shown, as can be seen in its FIG. 1, a wrap that applies compressive pressures against the patient's limb, forming interconnecting annuluses, as noted, and which are inflated. Generally, this particular compression device is for application to patients that are bedridden, for some time, and with the added pressure it is believed that assistance to blood flow may be enhanced, to reduce swellings associated with edema in the extremities.

The compressive sleeve to Hasty, shown in U.S. Pat. No. 4,091,804, shows a form of sleeve that is applied to the patient's limb, and subjects the same to compressive pressure, as a result of the injecting of compressive air into the various chambers, as noted, to provide compressive pressures against the patient's limb.

The patent to Annis, U.S. Pat. No. 4,207,876, shows a compression device with ventilated sleeve. This device may be applied, as for example, to the leg of a patient, to apply compressive pressures, during treatment. This device includes various openings to provide ventilation to the limb, during the application of this compression device, when used for treatment.

The patent to Kapp, et al, U.S. Pat. No. 4,256,094, shows an arterial pressure control system. This device utilizes a fluid pump for inflating a cuff, which functions, apparently, to provide arterial pressure, not too unlike that of the manual tourniquet.

The patent to Dillon, U.S. Pat. No. 4,269,175, discloses an apparatus that promotes the circulation of blood. This particular device, when applied, as for example, to the leg, and fluid pressure is injected into the same, as can be seen in its FIG. 1, is designed to enhance or provide intermittent external pressure pulses to the leg, to enhance blood flow, to and from the heart.

The patent to Villanueva, U.S. Pat. No. 4,374,518, shows an electronic device for pneumomassage to reduce lymphedema.

This device includes the fabrication of an outer boot, that may fit, for example, to conform to the human foot and leg, and utilizes a compressor to provide for successive inflating and deflating of the boot, within a preselected cycle, in order to stimulate fluid flow.

The patent to Arkans, U.S. Pat. No. 4,396,010, shows a sequential compression device. This device, as with those as previously described, is a pressure generating device for applying compressive pressures from a compressor against the patient's limb, through the use of a flexible, prepressurizable sleeve that encloses the limb and apparently pulsates pressure to the sleeve, and on to the limb, to enhance fluid flow.

The patent to Mummert, U.S. Pat. No. 4,408,599, discloses another complex apparatus for pneumatically controlling a dynamic pressure wave device. This device includes a series of longitudinal chambers that are subject to pressure inflation or deflation, by a dynamic pressure generating device, which is highly controlled by means of electrically operated components.

The patent to Siemssen, et al, U.S. Pat. No. 5,179,941, shows a contractile sleeve element and compression sleeve made therefrom for the peristaltic treatment of extremities.

The patent to Cariapa, et al, U.S. Pat. No. 5,437,610 shows another complex device incorporating various compression units, and pump means, which functions as an extremity pump apparatus.

The patent to Tumey, et al, U.S. Pat. No. 5,443,440, shows another form of medical pumping apparatus, in this particular instance, for application to the foot, and which can be inflated, in order to apply pressure to the foot, during its treatment for various impairment.

The patent to Peeler, et al, U.S. Pat. No. 5,575,762, shows a gradient sequential compression system and method for reducing the occurrence of deep vane thrombosis. This is a complex apparatus, for treatment as a therapeutic medical device and method for improving the venous blood flow within the patient.

The patent to Cone, et al, U.S. Pat. No. 5,591,200, shows another method and apparatus for applying pressure to a body limb for treatment of edema. This device is similar to the Reid sleeve, as previously reviewed.

The patent to Tobler, et al, U.S. Pat. No. 5,626,556, discloses a hook and loop attachment on a compression sleeve. This particular device also is related to the Reid sleeve type of apparatus, as previously explained, and does provide for the application of air pressure, into the lateral annuluses, as shown; to provide an inflated pressure against the foot, as can be noted, for the treatment of the patient's leg, and perhaps other extremities.

U.S. Pat. No. 5,901,393, describes the use of alternating pressures of large irregular shaped cells but the cells are in a design wherein successive rolls are stacked upon each other very tightly, and such inflation of a cell cuts off air flow to adjoin cells and produces a "duck billing". This patent was actually obtained to reduce "duck billing."

Another U.S. Pat. No. 6,154,907, upon a pneumatic cushion having individually deformed cells, as individual cell that can be deformed by a pressure sensor. Electrical signals are delivered to a controller in case the cell is deformed. There's no mention of Alternating pressure for relieving pressure points upon the body, especially when lying in a prone position for some extended length of time.

U.S. Pat. No. 6,711,771, upon an alternating pad, is an alternating pressure pad but it is for use for bladders, and not cells.

U.S. Pat. No. 6,823,549, upon alternating pressure cushion with inflatable lumbar support provides a structure with much larger cells, and there is spacing between adjoining cells to reduce or eliminate the duck billing. Because of this configuration, there are pockets in the pad that are a void of cells where tissue would not see inflation and deflation, in order to remedy pressure points upon the body.

U.S. Pat. No. 7,278,179, is upon an inflatable decubitus mat with vent structures controlled by heat sensors. It does include alternating pressure technology but radically differ as the cells vent as heat from the body trips a heat sensor. As the cells deflate, supposedly the body will cool down. The heat sensor then closes an opening on the cell and a pump inflates the cell once again.

Published application No. US 2004/0111048, is upon a compression device for chronic venous inefficiency. This is a device with an inflatable boot.

Application No. US2007/0113351, is upon a patients support apparatus having an air cell grid and associated method. This is a pad with individual air cells. The disclosure does not discuss inflation and deflation of the pad.

Published US application No. 2007/0249977, is upon a pressurized medical device. This appears to be more of a leg device for venous ulcers.

SUMMARY OF THE INVENTION

This invention relates generally to a portable form of compressive garment that may be selectively applied to various extremities of the body to provide for treatment of lymphedema and related forms of edema.

The lymphatic system of the body is actually a part of the human closed hydraulic system of circulation within the anatomy, that provides for sustaining normal physical function of the body parts, provides the proper displacement and movement of the various fluids, separate and apart from the circulation of blood within the body. As can be seen in FIG. 1, the location and functionality of the heart, lungs, the arteries, veins, and the other circulatory and vascular system of the body is compatibly associated with the extracellular lymphatic space. These lymphatic channels provide for transportation of lymph fluids to lymph nodes that remove various materials such bacteria and debris. Finally, the lymph fluid is discharged into the veins by way of the thoracic duct. Thus, this portion of the vascular system combats disease, by carrying away the deleterious bacteria and other infections elements that can cause problems to the body. In this FIG. 1, blood flowing into the small vessels (arterioles) entering the capillaries at that level, delivers nutrition to the intracellar spaces by ultrafiltration.

After depositing nutrients to the cells, the fluid traverses the extracellular space and is resorped in the venous end of the capillaries. However, only 90% enters the venous plexus and 10% flows into the lymphatics. The latter is profused through the lymph node basins (inguinal, axillary, intra abdominal and supraclavicular) and returned to the large veins at the left thoracic inlet via the thoracic duct. Thus, the fluid exchange that contributes to lymph formation originates at the microscopic level and is governed by Starlings laws of capillary function.

The subject matter of this current invention contemplates the formation of a compression garment that is selectively designed and manufactured to provide for application by the patient himself/herself. Once instructed, in proper placement it furnishes greater and more precise control, for treatment of the deleterious side effects manifested by and through lymphedema, as explained. In essence, the subject matter of this invention provides for the formation of an external compression device that may be applied to the arm, and embrace even part of the hand, or even extend upwardly into the region of the shoulder. Or, the sleeve may be especially designed for application to the leg, and extend down into the region of the ankle, and even embrace part of the foot, and extend upwardly towards the knee and thigh, depending upon the severity of the lymphedema being treated, and its location. Thirdly, the invention contemplates the formation of a further wrap, fabricated to the same principle as that of the previously identified sleeves, and which may embrace the upper thighs, and the lower abdomen, in order to provide the precise application of select pressure to the accumulation of body fluids, caused by lymphedema, manifested at these regions of the body. Adaptation for the thorax is also a possible option.

In essence, the appliance of this invention is formed as a flexible cloth, polymer, or related type of material, that has a series of grommets or seal points that form individual and smaller pressure chamber segments internally of the overall formed device. As grommets, placed 3 cm apart, provide for venting, from between the skin surface and the device, once installed.

In addition, there are one or more inflation or deflation valves, operatively associated with the internally formed compartments for the device, and in addition, the selective emplacement of the grommets, during formation of the device, furnish subsidiary chambers throughout the length of the formed device, so that multiple pressure points may be generated, within the inflated device, to apply multiple sites of pressure to the lymphedema that is subject to treatment. This strategic placement affects capillary pressures. The device is custom made, so that it may precisely fit not only upon the arm, leg, or the like, but has appendages that allow for the selective application of the device, for example, around the hand, under the thumb, so as to provide adequate coverage to all aspects of the limb subject to treatment, and afford a uniform application of pressure, through its various and multiple pressure points, to provide for a displacement of the edematous fluids, and their movement back into the circulatory system, in association with the adjacent lymphatic nodes, lymph vessels, and shifting of such fluids throughout the lymphatic channels, to reduce the undesired and frequently painful fluid accumulations.

In the formation of the device, at least a pair of layers of sturdy but flexible material, such as nylon, or other material that can be fabricated to provide for its inflatability, remain hermetically sealed, and be subject to significant pressures, while sustaining inflation, in order to function as an instrument for treatment of lymphedema, as previously explained. The precise location of the grommets, used to contiguously adhere the layers, at particular sites, but to allow for its inflatability, so as to form essentially three-dimensional diamond shaped pressure points. This allows increased venous flow by decreasing arteriolar hydrostatic pressure at these pressure points. These grommets, approximately three centimeters apart, more or less, afford a multiplicity of pressure points, upon the surface of the skin, thus reducing the lymphedema fluid, during usage.

Obviously, other dimensions for placement of the seal points, or grommets, may be considered, depending upon the degree of lymphedema being treated, and it is likely that the grommets may be located approximately one inch apart, or as much as five inches apart, depending upon the degree of pressure required, to sustain a uniform pressure over the entire surface being treated.

In addition, there are various inflation or deflation valves that may be added to the device, to allow for its inflation, and there may be a single valve, or perhaps valves that may locate approximately two to four inches apart, to allow for isolated injection of air into the device, during its inflation, once placed on the limb. The patient himself/herself may actually apply the device, by wrapping it, as an example, about the arm, and the hand, and secure the same in the position by means of any type of straps, such as Velcro hook and pile type tab connections, that may extend along the marginal edge of the device, and cooperate with a velour surface applied externally to the device, to furnish securement. Or, a series of Velcro or other buckle straps may locate along the margins of the device, and allow for a strap fastener of the wrap, about the arm, leg, or the like, once installed.

Any type of a pressure applying and generating device may be used, for inflating the device, such as a bulb type hand pumping and fitting means, of the type that is available from Haikey-Roberts Company, of St. Petersburg, Fla., and which is shown in its U.S. Pat. No. 4,744,391 and No. 4,998,582. These hand pumps, that incorporate their own fittings, may be pumped for injecting pressurized air into an encapsulated space, in order to inflate the same, or its opposite end incorporates a fitting that may be inserted into the inflation-deflation valves, to allow for a deflating of the device, after its usage. Other bellows type air inflating device may be used. Normally, the amount of pressure that is applied in the device of this type, and which has been found effective, is in the range of 35-45 mmHg, more or less. Thus, the amount of pressure applied is not too great, when it is compared with the amount of pressure that exists in the normal vascular system of the body, where a blood pressure may extend between diastolic and systolic ranges between 70-80 mmHg and 110-120 mmHg. On the other hand, the amount of pressure applied into this device, by means of a pressurized air injecting means, such as the bulb as previously explained, may be between the ranges of 5-10 mmHg, and upwards of 20-25 mmHg, or even as high as 40-50 mmHg, depending upon the amount of treatment required, and the form and extent of edema that may be present due to the magnitude of the lymphedema that exists.

In the practical application of the concept of this invention, in selective pressurizing of certain portions of a pad, it has been found that when select air cells in the pad whether it be air cells aligned in a row, or under the embodiment where the air cells under pressure points detect excessive pressure, that can lead to ulceration, and therefore need to be deflated, that the controller and pump of this invention will deflate those selective air cells, or a row of air cells, to within a range of pressure of approximately 0-5 mm hg. This calculates to approximately 0 to 0.0966 psi of pressure in any deflated cell. Obviously, other slightly higher pressure may still work just as well. And, where it needed to inflate select air cells, either in the adjacent rows, or in those region around the periphery of any air cell that has been depleted, because of its detection that too much pressure is be exerted upon the body at that location, that the surrounding air cells maybe inflated with pressure between a range of approximately 40 to 100 mm hg. This calculates to a range of approximately 0.7734-1.934 psi. Obviously, while the air cells in the experimental pad may be structured of approximately ½ inch in size, other size cells may be consider, and therefore, the pressures may be slightly increased, where the size may be of a larger dimension. These need to be taken into consideration.

Various other types of valves may be included in the structure of this instrument, within each segment of its formed multi-compartment wrap, so that each segment may be individually filled with air, under pressure, to the amounts as previously reviewed, necessary to treat the degree of lymphedema that has been generated within the limb at that contiguous location. For example, various types of shut-off valves, one-way check valves, and valves that may be manually opened, to provide for release of pressurized air, are readily available from a variety of sources. For example, Colder Products Company, of St. Paul, Minn. 55114, manufactures and markets a variety of various types of valves, check valves, release valves, and couplings, for use for the application and release of air, under pressure, to medical instruments. In addition, the Martin-Weston Company, of Largo, Fla. 33770, manufactures and markets inflation pumps that may be applied to the foregoing type valves, to allow for the injection of air under pressure into the segments of this garment, during its installation and usage. On the other hand, instead of utilizing a manual type of pump, there are many more expensive type of pumps, valves, seals, and the like, that are available from a variety of sources, such as the fill and drain closures that are available from a company such as Halkey-Roberts Corporation, of St. Petersburg, Fla.

Furthermore, in order to determine the degree and amount of pressure applied into each segment of this garment, hand-held type of digital manometers may be used, and applied to the valves after or during the injection of air, to provide for an immediate digital readout of the amount of pressurized air that has been applied into each segment of the garment, so that more precise levels of pressure can be generated, at select locations along the length of the garment, as applied to a limb. Such hand-held manometers are available from Dwyer Instruments, Inc., of Michigan City, Ind. 46361, amongst other and a variety of sources.

In addition, in lieu of the use of a manometer, attached to the valves or to the segments of this wrap, it is just as likely that a form of pressure transducer may be utilized within each segment of the wrap, detect the amount of pressure generated therein, convert it to a charge, and transfer it to a readout, upon the surface of the segment, where the generated pressure may be readily observed. Such transducers may be obtained from Linton Instrumentation, of Diss, Norfolk, U.K., under Model No. SensoNor 840. For example, an LED readout that may display the quantity of pressure generated could be provided upon the surface of each segment, to let the physician and medical technician know the exact amount of pressure generated within each segment, during usage and application of the wrap. Also, if the patient utilizes the garment at home, through self service, this would provide a ready readout as to the amount of pressure pumped into each segment, during usage and application, so the patient may be quite precise in the amount of pressure developed within the wrap, in accordance with the specifications from the doctor, instructing regarding its usage. Furthermore, the pressure transducers may be incorporated into the inner surface of the wrap, or applied upon that surface of the wrap that is applied directly to the affected limb, so that an exact reading of the amount of pressure generated upon the surface of the limb subject to lymphedema, may be readily determined, upon usage of this particular garment.

Obviously, the type of material used as previously referred to in forming the multi-layer device, that exhibits the internal chambers that are fabricated to provide for the multipressure points from the device, when used, and may include those materials as previously described, while the internal surfaces of the liner may be treated, to make it hermetically sealable, or it may include an internal liner of a polymer, such as polyethylene, to assure that the device, during usage, will be pneumatically leak proof.

In addition, and in the case of the device as manufactured for use upon the arm, it may extend and wrap around the palm, leave clearance for the fingers and thumb. It may provide integral wrapping about the wrist, forearm, elbow, biceps, and even extend up into the region of the shoulder. Or, the device can be formed of a shorter dimension, depending upon the localized need for treatment. In addition, it may be formed for wrapping about the leg, the thigh, down to the ankle, and even about a portion or all of the foot, depending upon the severity of the lymphedema, and the type of treatment required. And, as previously explained, the device may be fabricated for wrapping about the lower abdomen, and have a connecting portion that may wrap about, individually, each of the upper associated thighs, to provide a localized treatment at that region of the body, which can frequently manifest lymphedema that requires treatment as such swelling may result from radical surgery that is done for cancers in the pelvic organs, such as the uterus, ovaries, rectum and prostate. Radiation of this region can also cause sclerosis of lymphatics resulting in edema.

It is, therefore, an object of this invention to provide an appliance for use for treatment of lymphedema that is light weight, very portable, washable, and easily applied, even by the patient alone.

This invention also contemplates the formation of various shaped pads, that may have pressure regulated at various segments around its perimeter, and which can be controlled furnishing selective pressure within this of the pad segments, so that support for the body may be provided at select areas, and less support elsewhere, where pressure is undesired. For example, where bed sores may be present, it is desirable that the pad will be less pressurized, and provide less force upon the infected area, but that the surrounding pad segments will be inflated to a higher pressure, to maintain the elevation of the surrounding body to provide for that regulated and controlled support. It is likely that this type of a pad could be formed as just that, a rectangular or square pad, for use upon the operating table, or upon the hospital bed, under the patient, regulate the amount of support provided for the body through usage of the pad, in order to better treat various infections, and decrease their undesirable results, when a pad or mat of this type is employed. Furthermore, the pad may be designed to fit over the entire mattress of the hospital bed, or bed at home for the patient, for that matter, but may be formed as smaller dimensions of pads for locating under select areas of the body, particularly those that are under treatment. In addition, the pads may be designed shaped as for example for setting upon, but furnishing less pressure at select areas for reasons as previously described.

It is known in the medical filed that the capillaries carrying blood, from the arteriole to the venule of the lymphatic vessels, is subjected to various pressures, and place pressure upon the tissue, or tissue fluids that accumulate, and such intravascular pressures can have an effect upon the proximate body parts, such as the skin or tissue, and this can all lead eventually to infection, bed sores, or the like. Thus, through the usage of a mat of this current invention, the types of pressures exerted, and therefore, arteriole and venule pressures, in addition to the colloid osmotic pressures, can be somewhat regulated when subjected to various pressures externally, that they have a tendency to reduce the incidents of unwanted scars, which may otherwise cause infection, if exposure is due to last for any extended period of time, which may also give rise to infections, such as bed sores, and the like. The subject matter of this current invention is designed to elevate and help control these types of portions of the body.

The benefits of usage of the current invention can best be understood by reviewing the changes and pressure that occur as the pad of this current invention is deflated at a detected pressure point, and then inflates the pad at adjacent locations, so as to take the weight off of the pressure point subjected to too much pressure. For example, as can be seen in FIGS. 21a and 21b, these show the before and after inflations/deflation cycles, of the pad, and its effect upon the pressure on the body, as can be noted. For example, in FIG. 21a, it can be seen that the pressure applied at the shoulder blade area S (Scapula), the lower back area B, and the area under the head H, exhibit much greater pressure as the patient lies for an extended period of time during treatment, and operation, or the like. But, in FIG. 21b, it can be seen that the pressure points at the Scapula $S_1$, and lower back $B_1$, have substantially reduced, because the pressure of the pad at those locations have been lessened, and the adjacent portions of the pad have had increase pressure applied to them, which has a tendency to relieve the pressure upon the body parts as previous described, as with respect to FIG. 21a. Hence, these pressure studies demonstrate that a constant computerized change of the pressure points on a body lying in one position, such is where the pad is applied in the operation room, or on a wheelchair, due to the operations of the pad, by detecting excessive pressure points, and reducing pressure at that location, while increasing the pressure in surrounding areas, prevent fluid accumulation by milking the fluids and nutrients to and from the boney prominences of the body, where the pressure ulcers frequently occur. Through the usage of this current pad, these pressure points are varied, the pad is sensitive to the generation of excessive pressure points, and automatically reduces the pressure at that area, and increases the pressure in the surrounding area, for pressure relieving purposes.

By way of example, where pressure maybe applied within a particular segment of the pad at a point where excessive pressure is applied onto a particular portion of the body, such as at the scapula, or at the back area, such as where pressure may be applied within the range of 1 psi to 3 psi, or range that may have a tendency, over a period of time, to commence the generation of pressure ulcers at those locations. This can be seen in FIG. 21a. But, by relieving the pressure at those pressure points, by reducing the pressure in the segments of the pad within these regions, for example, down to approximately 0 psi to 0.10 psi, but increasing the pressure in the segments of the surrounding areas, up to a higher pressure, such as in the range of 0.77 psi to 2 psi, this lessen the pressure at the previous pressure points, upon the body, and increases the lift upon the body in the surrounding areas, to thereby reduce the incidence of generation of any pressure ulcers, at these identified pressure points. This is essentially what has been done in FIG. 21b, in order to lessen the pressure at the locations of the identified body parts. And, by alternating these pressures, for example, maintaining the lower pressure within the vicinity of the identified body parts for a period of time from 5 minutes to 15 minutes, and increasing the pressure in the surrounding areas at the same period of time, and then alternating these pressures for a period of time, such as maintaining the higher pressure for 5 minutes at the scapula and back, before lowering the pressure an additional 15 minutes, has a tendency to prevent the generation of too much pressures upon these body parts, and substantially reduces the incidence of the generation of pressure ulcers, or bedsores, as explained. Hence, the concept of the invention is to lower pressure at the pressure points upon the body, where pressure ulcers pressure ulcers may generate, and elevate the pressure in the surrounding areas, or segments of the pad, in order to reduce the incidence of bedsores. In a further embodiment for this invention, it is just as likely that the pad will be formed of longitudinal segments, so that as one segment is lessen in pressure, the adjacent longitudinal segments will be elevated in pressure, and these defined pressures being alternated, time wise, as for example, every 5, 10, or 15 minutes, so as to keep varying in the pressure points upon the body, and lessen the potential for developing bedsores upon the patient.

Another object of this invention is to provide a lymphedema treating device that includes a series of perforations, at the region of grommets, or seals, which provides two beneficial results. One, which allows the access of air to the underlying and wrapped skin during usage of the device, but secondly, includes a series of seals, at these locations, which afford the generation of air pockets. This series of grommets produce a multitude of pressure points internally along the entire length and circumference of the applied sleeve rendering variable pressure on the capillary beds.

A further object of this invention is to provide a pressure grommets that allows for its generated pressures, internally, during usage, to be precisely controlled, even by the patient during application and usage. LED pressure sensors provide this information.

Still another object of this invention is to provide a much less costly type of appliance, for treating lymphedema, than currently in use.

Still another object of this invention is to provide a pressure grommets that incorporates at least two fail-safe features, one is in a valve or valves that allows filling only a certain pressure, and/or an appliance that fills the air chambers that only allows a maximum pressure of up to 45 mm of mercury, or slightly there above, and certainly below such level as could be harmful.

Still another object of this invention is to provide for a pressure garment for use for treating lymphedema that is easily and quickly applied to the effected limb.

Yet another object of this invention is to provide a pressure garment that is durable.

Still another object of this invention is to provide a device for treating lymphedema which is very compact, as during nonusage, and is very accommodatable for travel, when required.

Another object of this invention is to provide a very simple design that is safe in its application, installation, and usage.

Yet another object of this invention is to provide a pressure garment which when applied can aid towards decreasing post-operative edema and thus decrease post-operative disability and enhance the healing of a wound.

Another object of this invention is to provide a lymphedema treating device that may facilitate and be of help to the patient after orthopedic surgery, any surgery, or even during post-operative vascular surgery healing in the extremities.

Yet another object of this invention is to provide a somewhat flexible, inflatable edema treating device that will further act as a support that may even function somewhat as a cast to limit the amount of flexion of a limb, but yet, have sufficient flexibility to allow the limb to attain some movement, during usage.

Another object of this invention is to provide a garment for use for treating lymphedema that may be manifested, usually after surgery, in various limbs of the body, such as along the arms, in the lower reaches of the legs, at the thighs, or even in the vicinity of the abdomen, and unless treated, results in a buildup of significant accumulation of bodily fluids that are unsightly of appearance, but more specifically, detrimental to the continuing health or recovery rate of the patient. A body wrap may be beneficial in burn treatment also.

Another object of this invention is to provide a pad or mat that may have regulated pressures applied to select areas within its structure, so as to vary the amount of pressure exerted upon the contiguous body parts, under or to which this pad is applied.

A further object is to provide a pad that can provide regulated pressures to select areas of the pad for select periods of time, and alternate these pressures whether it be less pressure at one location, or increase pressure at an adjacent location, whereas to vary the extent of pressure points generated upon select areas of the body over an extended period of time.

These and other objects may become more apparent to those skilled in the art upon reviewing the summary of this invention, and upon undertaking a study of the description of its preferred embodiment, in view of the drawings.

BRIEF DESCRIPTION OF THE DRAWINGS

In referring to the drawings, FIG. 1 provides a schematic view of the human closed hydraulic system of circulation of both vascular and lymphatic fluids depicting the formation of lymphatic fluid in the extracellular space.

FIG. 3 is a plan view of the compression garment, during nonusage, as shown in FIG. 2;

FIG. 4 is a sectional view of the arm applied garment, taken along the line 4-4 of FIG. 2;

FIG. 5 is a view of a modified form of garment, that extends up to and onto the shoulder of the patient, from the vicinity of the wrist, for applying selective and controlled pressure along the length of the arm, to treat edema;

FIG. 6 is a view of the application of a modified garment to the thigh, leg, and ankle of the patient;

FIG. 8 is a plan view, or open view, of the modified garment shown in FIG. 7;

DESCRIPTION OF THE PREFERRED EMBODIMENT

Figure 1:
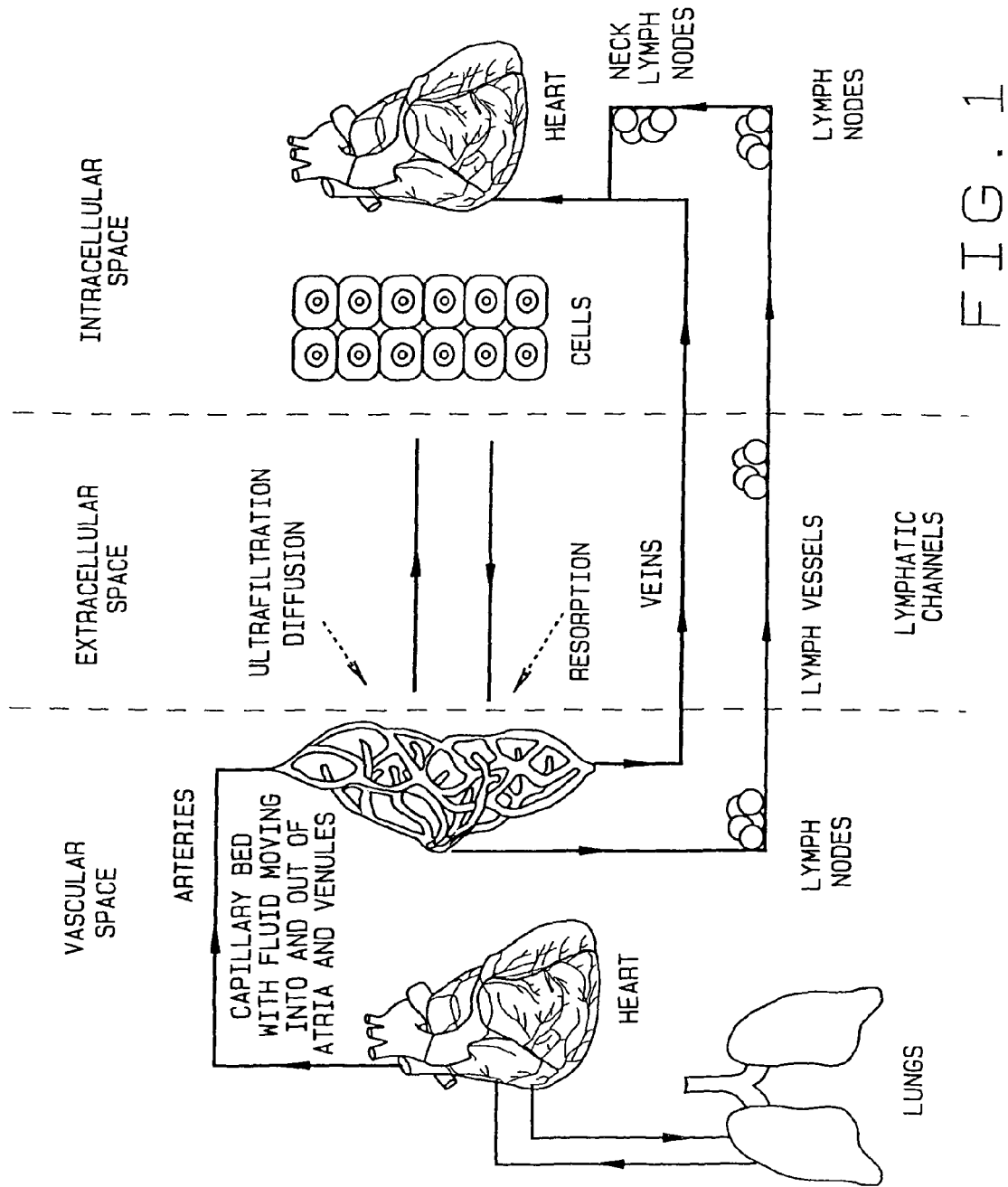
Figure 2A:
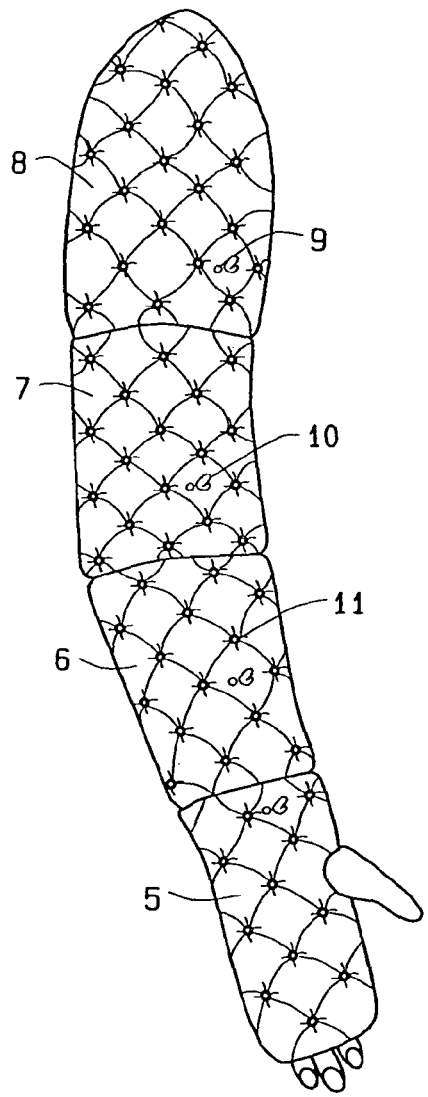
FIG. 2 provides a perspective view, both in the lateral view, and the medial view, of the compression garment of this invention applied about the lower arm and hand of the patient.
Figure 2B:
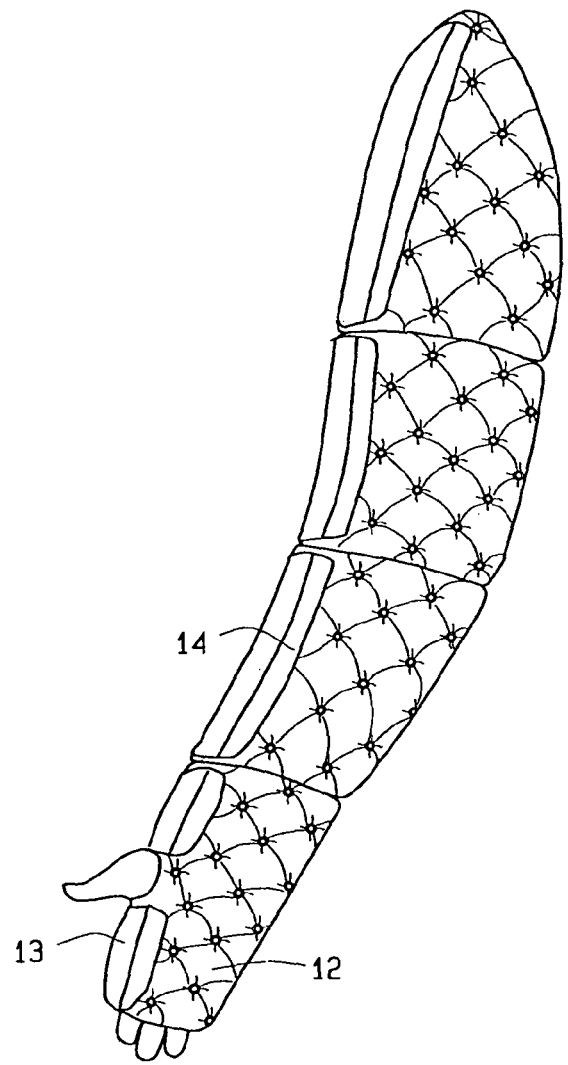

In referring to the drawings, and in particular FIGS. 2 through 4, the compression garment G of this invention is readily disclosed. In this embodiment, it is applied to the forearm, about the wrist, and embraces part of the hand of the wearer or patient. The garment, as can be noted in FIG. 3, comprises and is formed of a flattened configuration, including upper and lower layers 1 and 2 of a fabric-like material, such as nylon, or any other hermetically sealable type of cloth, polymer, or flexible material, and which can be inflated to sustain pressures of air or other fluids to the amounts as previously summarized. As can be seen, the two layers of material are sealed together, by means of a series of grommets 3 throughout their extent, and which provide for segmented pockets, as at 4, of air that provide for a generation of point pressures, to the treated arm, as previously explained. The object for forming these various air pockets, along the length of the compression garment, and as previously summarized, is to provide the application of a very controlled pressure, at spaced and isolated locations, to the edema effected limb. At the same time avoiding the application of tourniquet type pressure, throughout the extent of the limb to which the garment is applied, so as to not curtail or shut off the vascular functioning in the effected area. Thus, blood flow in subcutaneous and fluid migration, during the application of the device's controlled pressure, will cause accumulated fluids to continue their circulation, but reduce their accumulation, to attempt to place the affected limb back into its normal processing, normal appearance, and to avoid the deleterious and impairments that may be generated in the limbs, because of the accumulation of the endemic fluids.

The compression garment may be a continuous length of the material, and liners, forming the length of the garment, and be inflated between its various grommets to form the identified pressurized air pockets, or as shown in FIGS. 2 and 3. The garment may be segmented, between the various segments 5 through 8, and be individually inflated, by means of their respective valves (10), as can be noted. These valves (10) are provided for both inflating of the garment, or its individual segments, or it can be used for discharging and deflation of air, for either greater proper control of the amount of pressure applied, or for removal of the garment, after treatment.

In addition, the various grommets 3, as can be seen, have apertures, as at 11, within their interior, so as to allow for any captured air, between the garment and the surface of the limb skin, to escape, and which would otherwise, or may, provide a variation in the amount of pressure desired, when inflating the garment during usage.

As can also be seen, various types of sensors, as at 9, may be installed into the layers forming the surface of the garment, and be sensitive to the amount of pressure being added into the various segments, to provide a ready indication and readout of the amount of pressure applied, so the medical practitioner, or even the patient alone, can readily determine whether adequate and proper pressure levels have been reached, during treatment. Furthermore, various types of microchips, or LED indicators, may be associated with the sensors, and provide a digital, or either analog, readout of the amount of pressure generated within the garment, and its various segments, during usage and application.

In order to provide for the uniformity for the product, and to add to its appearance, it is likely that a covering sheet, such as one shown by way of example at 10A, of the same or different material from which the segments of the wrap are formed, may overlap each of the valves 10 and sensors 9, so as to form means for covering these elements, during usage of the wrap. One edge of the cover may include a hook and pile fastener type of connector, so that the cover may be secured in place, once installed, or pulled free, to expose the valve or sensor, accordingly. See FIG. 3.

Structural wise, the garment, being previously described as being fabricated of at least a pair of layers, will extend the length of the limb to which it is applied, and as shown in FIG. 2, in that embodiment, extends up to approximately the elbow of the wearer. At its opposite end, the garment may be designed and fabricated, to include sufficient length to override most of the hand, up to the position of the fingers, including a segment at its opposite width, as at 12, which may embrace the palm of the hand, and cooperate with an appendage, as at 13, that extends down across the hand, between the index finger and the thumb, and for connection to the portion 13 of the shown garment. Furthermore, the edges of the garment may include, as along the inner surface along one edge, a segment of hook or pile fastener, such as fabricated from Velcro, as can be seen at 14, while the opposite edge, as at 15, upon its undersurface, may include the other segment of Velcro, as at 16, for securement with the defined edge 14, and allow for the garment, when wrapped, to snugly embrace the limb of the wearer, during treatment. Obviously, other types of fasteners can be utilized, such as clasps, one or more buckles, or any other type of means for securement of the edges of the garment together when wrapped around the limb of the patient.

In addition, any type of pump means, such as a bellows device, or bulb (not shown), or the like, may be applied to the valves 10, and facilitate the pumping of pressurized air into the garment, after installation, and in preparing it for treatment. Likewise, any type of release valve, incorporated into the structure of the valves 10, and which may be manipulated, to allow for discharge of air, will be applied thereto, in order to allow the patient to deflate the garment, and remove it, after treatment. These types of valves are readily known in the art, and are available for this type of adoption, installation, and usage.

As can be seen in FIG. 5, the garment G1 is modified, and will extend from the wrist of the patient, up to and over the shoulder, to allow treatment along the extent of the shown limb, as can be understood.

Figure 7:
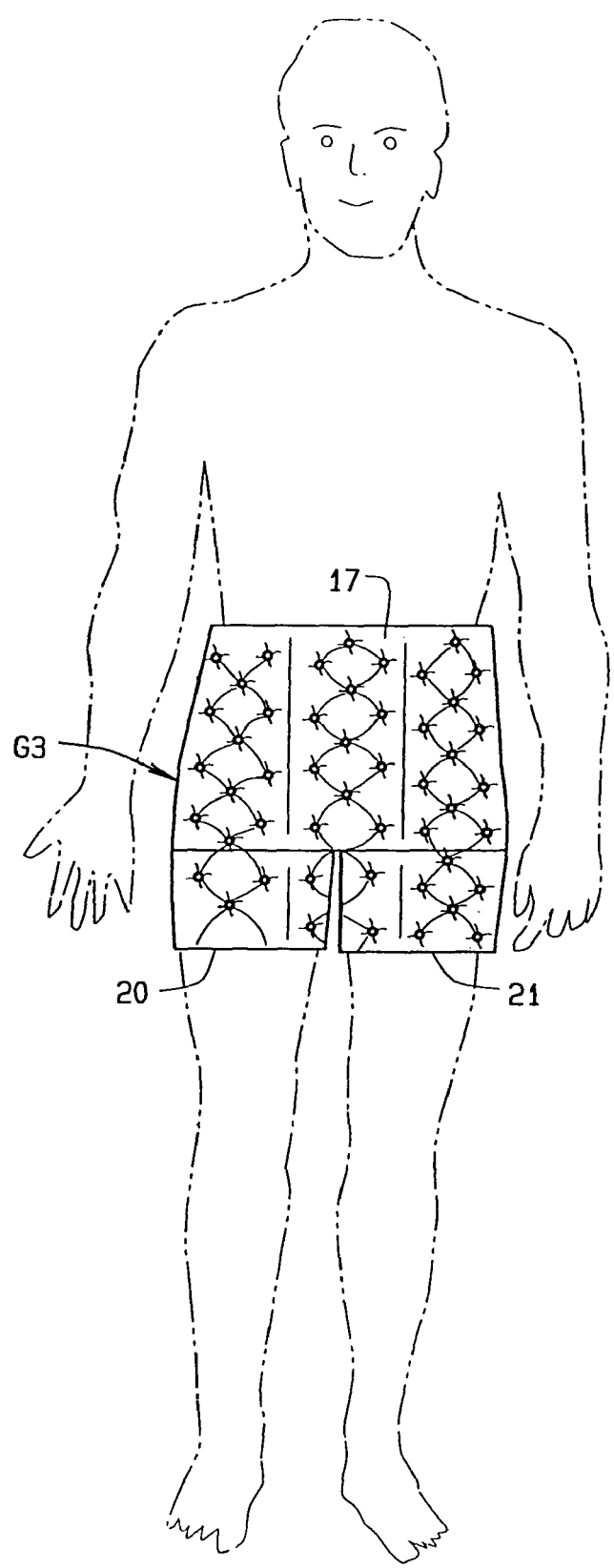
FIG. 7 is a view of a modified garment of the type that is applied at the vicinity of abdomen and upper thigh of the patient to provide edema treating pressure at these vicinities of the body.

In addition, as can be seen in FIG. 6, the Garment G2 may be further modified, and extend from the thigh, all the way down to the ankle, and even wrap about the foot, and readily available for inflation, to function to treat edema, that may be caused at these locations. Or, the leg wrap may extend simply down the calf, and embrace the ankle, and foot, as an alternative. Furthermore, as can be seen in FIG. 7, the garment G3 may be applied to the abdomen, waist, and upper thighs of the patient, for treatment of edema thereat. As noted in FIG. 8, this style of garment will have a waist embracing portion 17, with the usual fasteners 18, as previously explained, applied to either end, and in addition, will link by means of an appendage 19 to the upper thigh embracing components 20 and 21, which also include their various fastening means 22, about the upper leg of the patient. Nevertheless, and regardless what shape or configuration the garment undertakes, in its assembly and manufacture, it will include various upper and lower layers of material, that are hermetically sealed, and which include a series of grommets or other means for fastening of the layers of material together, to form those isolated pillows or segments to form pocketed pressurized air, for treatment of the affected limb, when applied. In addition, and while the terminology grommet has been used herein as means forming these pockets, obviously, these could be simply seal points, that connect the two layers of material together, regardless whether they include the apertures 11 therethrough, as previously explained for preferred embodiment.

As previously reviewed, the essence of this invention is to provide for a lightweight and washable type of garment, that can be applied to various affected limbs, even by the patient, himself/herself, to attain treatment, as required, or prescribed. It provides for controlled application of pressure, at various points along the treated area, in a manner that does not disrupt the desired and normal biological function of the vascular and lymph systems of the body, particularly at the treated area. In addition, the garment is relatively small, flexible, is very compact for folding, easy to take when traveling, so that treatment can be undertaken anywhere, and not just at the hospital, medical facility, or the doctor's office. It can be done at home, or even on a business trip, as necessary. The garment has sufficient flexion, so that the limb, to which it is applied, can still be used, or manipulated, even during treatment.

Figure 9:
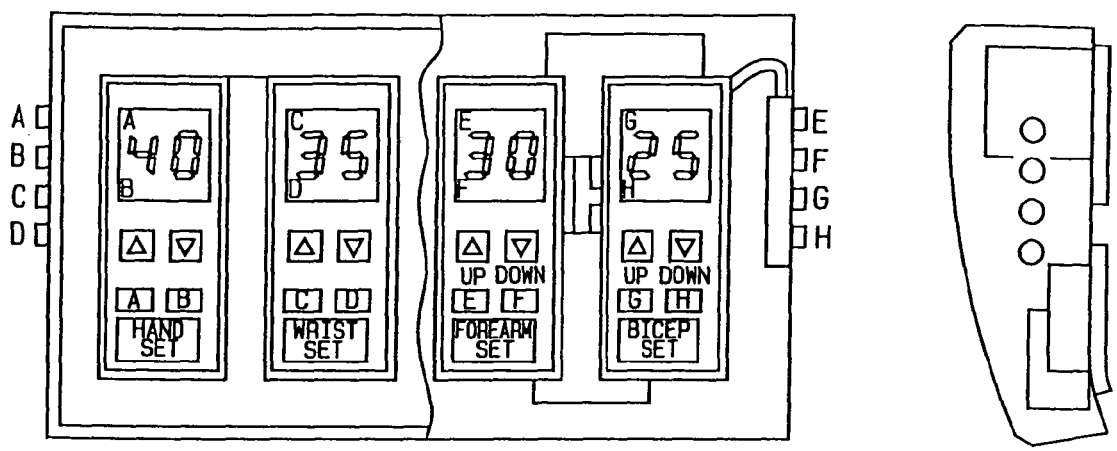
FIG. 9 is a schematic view of the front face of the electronic controller that is used for regulating the quantity of pressure added to or removed from various segments of the sleeve, during its usage.

FIG. 9 discloses the electronic controller, or at least provides a schematic of its front face, showing how various pressures are detected, determined, and used to automatically adjust the amount of air pressure pumped into the various segments of the sleeve, during its operations. Advancements in electronic circuit miniaturization now make it possible to develop a device that can control these pressures, be battery or otherwise operated, they are light weight, add significant safety features and allow for an individual complete freedom to move about and continue in their normal daily routine or sleep in complete comfort. The electronic controller automatically monitors the pressure at each section of the sleeve and verifies that it is set correctly. If, in the case of an arm sleeve, the patient should bend the arm, the sleeve would increase pressure in that section, and the controller would automatically vent that section of the sleeve back to its set point. When the patient straightens the arm, the pressure would reduce and the miniature pump inside the controller would automatically increase the pressure to the original set point.

Figure 10:
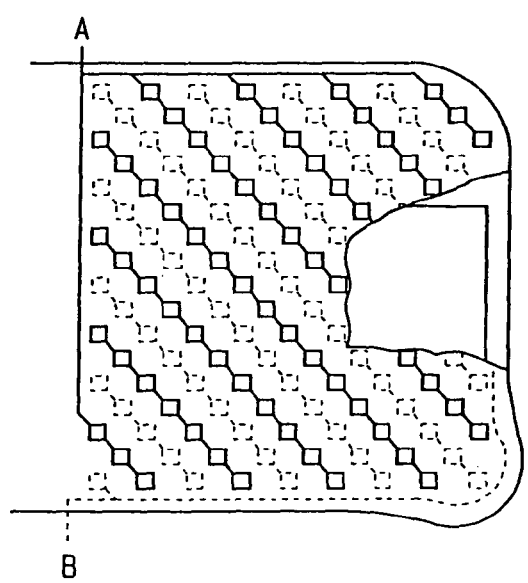
FIG. 10 provides a sectional view of the hand section of the sleeve, showing the various raised air pockets, the circuit lines leading to select of the air sections of the sleeve, which provide for a sensing as to where pressurized air must be added, or subtracted, in order to equalize the pressure of the sleeve upon the limb being treated.

As can be noted in FIG. 10, there are circuit leads that have sensors that are responsive to the amount of pressure at the various segments of air pockets, and can determine when pressure is becoming excessive and thereby should be reduced, or when pressure is lightening, and therefore, air should be supplied and pumped to the pocket to add pressure at select locations. This controller has several additional significant uses when used in conjunction with this sleeve devise. One, the pressures can be adjusted periodically on a prescribed time table to dynamically work the skin surface. Secondly, the advance designs of the sleeve could incorporate twin bubble cell circuits in each section so that a constant alternating pressure in each cell circuit would result in a therapeutic massage of the afflicted area resulting in a potentially greater overall fluid reduction.

Figure 11:
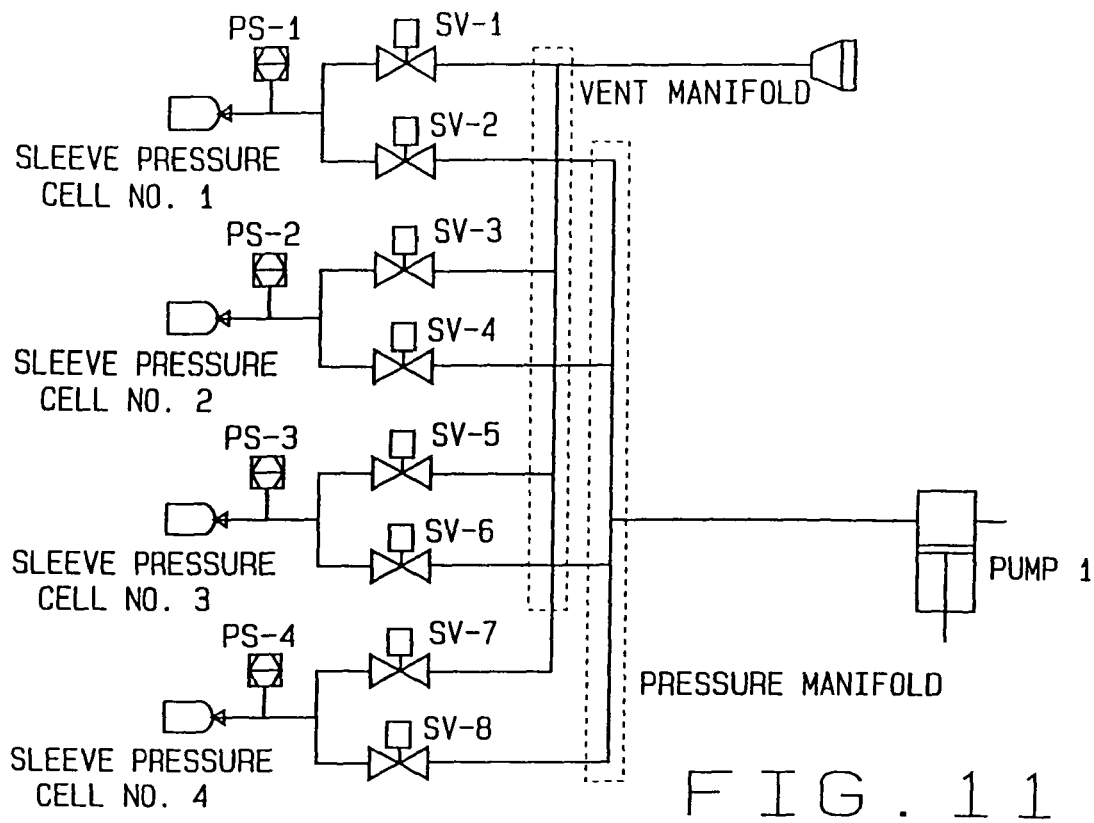
FIG. 11 provides a sleeve pneumatic schematic.

FIG. 11 discloses the lymphedema sleeve and the pneumatic schematic for the compression garment of this invention. As disclosed, the system is composed of a single DC powered air pump, as noted at pump 1, and includes eight solenoid valves, as noted. Each of the four compression cells, of the preferred garment, is continuously connected by way of tubing to a dedicated pressure transducer, generally identified as PS-1 through PS-4. The pump is connected to a manifold, which feeds each cell via a dedicated solenoid valve, as noted. Each compression cell is provided with a dedicated solenoid valve for venting its particular cell. The system is capable of independently pressurizing and venting each compression cell. Variable pressure set points can be independently set for each cell. Fill rates will be impacted by set point pressure and the number of cells that are to be filled. The unit is capable of simultaneously pressurizing a cell(s) while venting another cell(s). Custom pressurization and massage can be implemented. The system will be able to quickly reduce pressure to ease bending the sleeve at the knee/elbow joint.

This system is capable of simultaneously performing in a desired operation, such as pressurization, static, or venting, on each of its separate compression cells.

Because of the necessity, in the event that the compression garment is designed incorporating four cells, of including eight solenoid valves within the structure, the cells and the garment will require a little more size, in order to accommodate such componentry.

Figure 12:
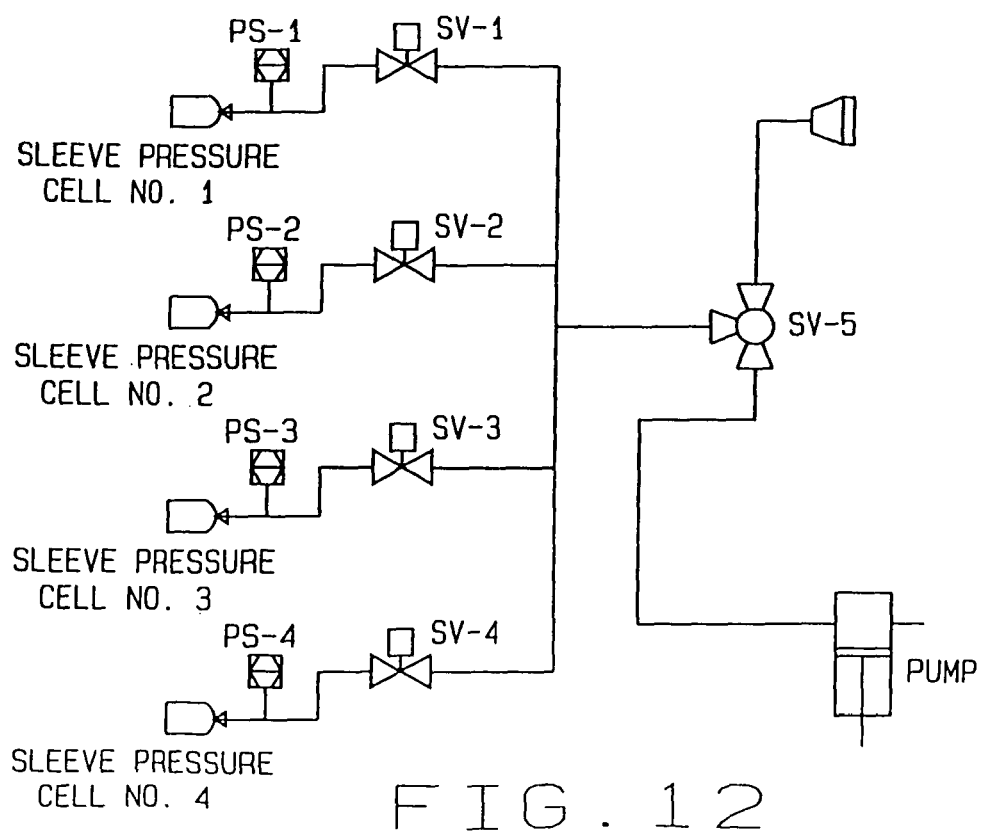
FIG. 12 provides a further modification to the sleeve pneumatic schematic.

On the other hand, the modification for the lymphedema sleeve pneumatic schematic as shown in FIG. 12 reduces the number of solenoid valves used. This system is composed of a single DC powered air pump and five solenoid valves. Each of the four compression cells is continuously connected via tubing to a dedicated pressure transducer. Each compression cell is provided with a dedicated solenoid valve for controlling the pneumatic access to the cell. A common manifold connects each cell control solenoid valve with the common port of a 3-way solenoid valve, as noted at SV-5. The normally open port of the 3-way valve is connected to the pump, and the normally closed port is connected to vent, as noted.

The system is capable of independently pressurizing or venting a specific compression cell. The unit will not be capable of simultaneously pressurizing a cell(s) while venting another cell(s). Variable pressure set points can be independently set for each cell. The fill rate will be impacted by set point pressure and the number of cells that are being filled. Custom pressurization and massage profiles are possible, but they will be limited by the inability to pressurize a cell while simultaneously venting another cell. The system will be able to reduce pressure to ease bending the sleeve at the knee/elbow joint, but the response time will be slower than the schematic as shown in FIG. 11.

The benefits of this particular system is that it is capable of performing any desired operation, i.e. pressurization, static, or vent, on each compression cell. The limitation of this particular system is that it can simultaneously fill or vent one or multiple cells. But, it can not do so at the same time. As a result, the system may have a desired state delayed until completion of the current cycle or state.

Figure 13:
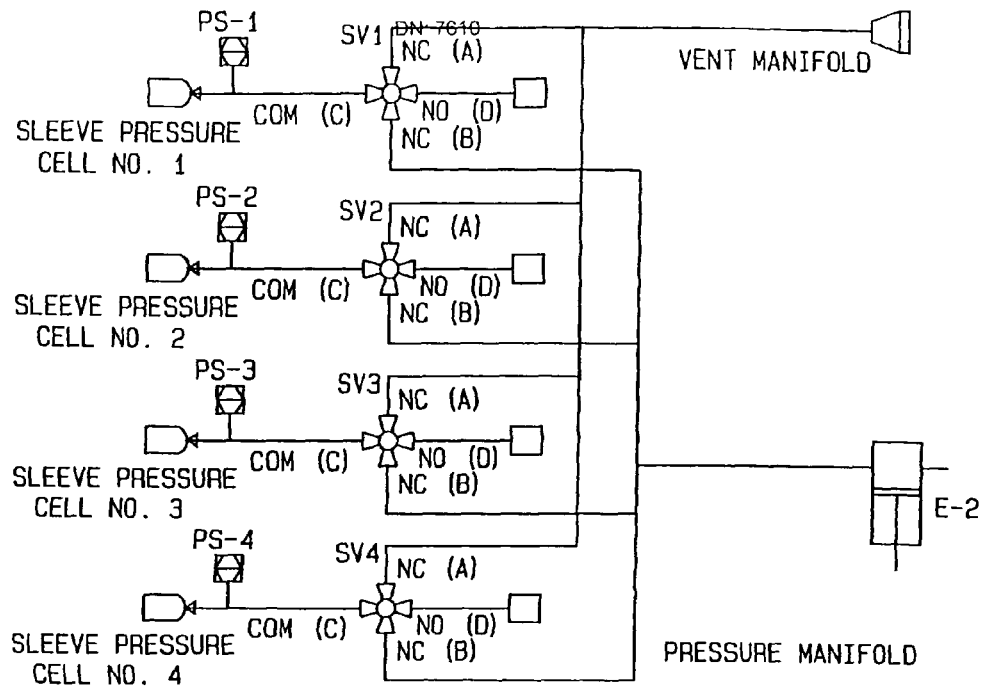
FIG. 13 provides a modification to the sleeve pneumatic schematic.

A further modification to the subject matter of this invention is shown in the system disclosed in the schematic of FIG. 13. This system is composed of a single DC powered air pump and four solenoid valves. Each of the four compression cells is continuously connected via tubing to a dedicated pressure transducer. Each compression cell is provided with a dedicated 3-position solenoid valve for controlling pneumatic access to the cell. The solenoid valve is comprised of two solenoids in three positions. The port position C is the common connection. Port A is a normally closed port that is connected to the common port C when the signal is applied to solenoid A. Port B is a normally closed port that is connected to the common port C when a signal is applied to solenoid B. Port D is the normally open port that is connected to port C when no signal is applied to solenoid A or B. Port C of the valve is capped. Port A is connected to the vent manifold. Port B is connected to the pump manifold. Each cell can be independently connected to the vent manifold, the pump manifold, or closed off.

This system is capable of independently pressurizing or venting a specific compression cell. Variable pressure set points can be independently set for each cell. Fill rate will be impacted by set point pressure and the number of cells that are being filled. Custom pressurization and massage profiles are possible. The system will be able to reduce pressure to ease bending the sleeve at the knee/elbow joint, and response time will be similar to the design option as set forth in FIG. 11.

This system is capable of performing any desired operation, such as pressurization, static, or vent, on each compression cell.

Figure 14:
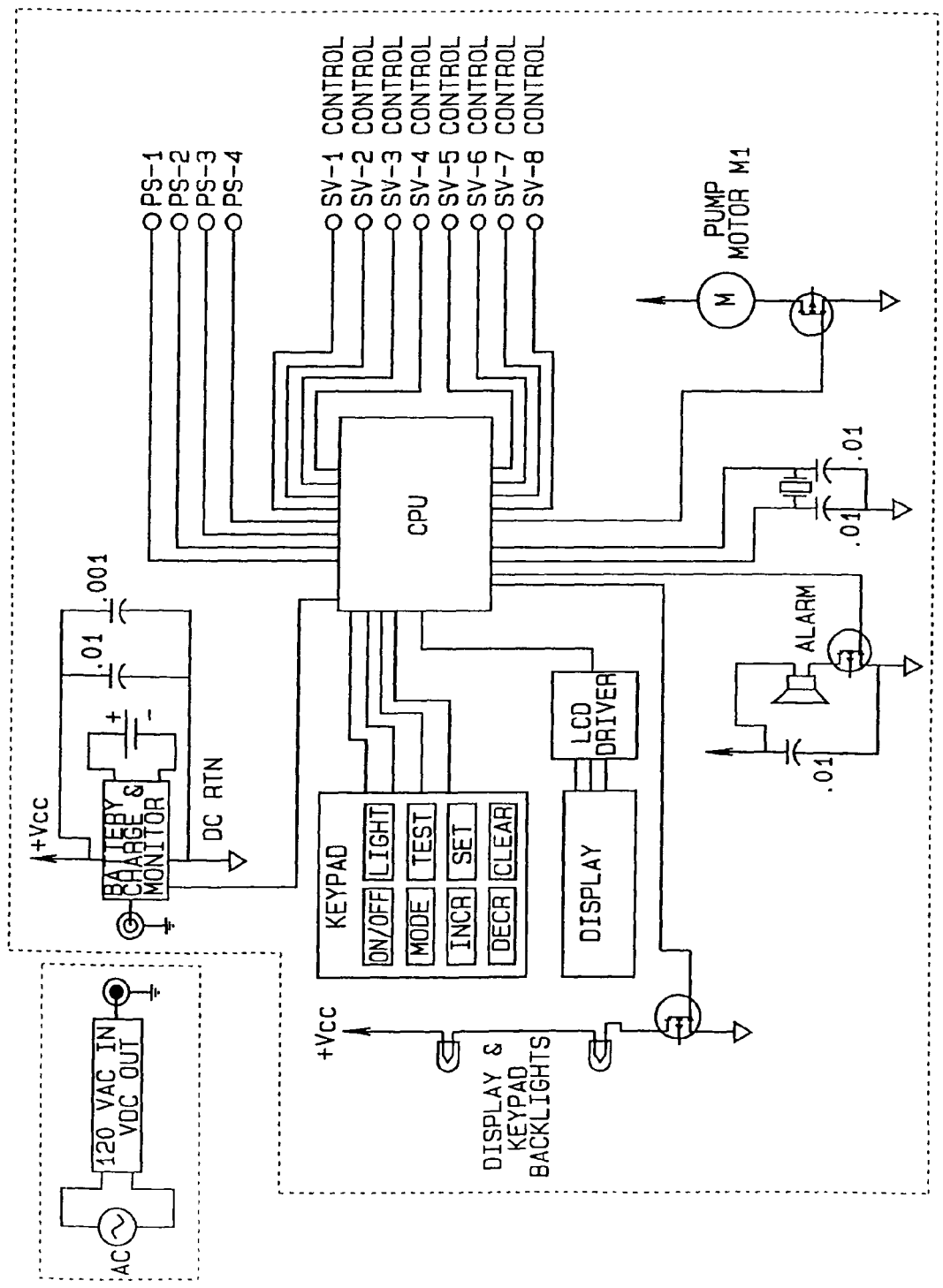
FIG. 14 provides a schematic of the electrical circuitry and the microprocessor controller and monitors for the compression garment of this invention.

Electrical schematic for operation of the electrical-pneumatic and solenoid controlled valves for the compression garment of this invention is shown in FIG. 14. As noted, power of the system is capable of operation from a rechargeable battery source, or DC power, provided by a standard 120 VAC volt wall adapter. The control includes the battery charge circuitry and battery state monitoring circuitry. The monitoring circuitry includes an alarm output to the microprocessor controller.

The display, as noted, is a backlit LCD display that provides control setting and operating parameter information to the user. The keypad, as noted, is a sealed multi-switch keypad which provides operator interface with the unit. The alarm, as also noted, is a Pizeo-electric audio alarm that provides audio indication of controller faults. The faults will include the low battery, cell over pressured/under pressured, pump fault and pressure sensor fault. The pump is a DC-powered pneumatic pump that provides pressurized air to the compression cells. The pump is controlled by a digital signal from the microprocessor, or CPU. The manufacturer of the CPU being Motorola, Inc. of Austin, Tex., Model No. 68HC16, or the manufacturer may be Microchip Technologies, Inc. of Chandler, Ariz., Model No. PIC8F4320. The microprocessor sends a signal to a FET transistor that provides low side switch control of the pump motor.

The solenoid valves, generally identified at SV-1 through SV-8, are used to control the pressurization and venting of the compression cells, for the garment. The valves are controlled by a digital signal from the microprocessor to a FET transistor that provides low side switch control of the valve solenoid. Solenoid valves are bio compensated to minimize the effects of switching transients.

The pressure sensors, as indicated at PS-1 through PS-4, provide a temperature compensated DC signal to the controller microprocessor. The system includes a sensor for each compression cell. The sensors can be mounted on the sleeves or internal to the control unit.

Figure 15:
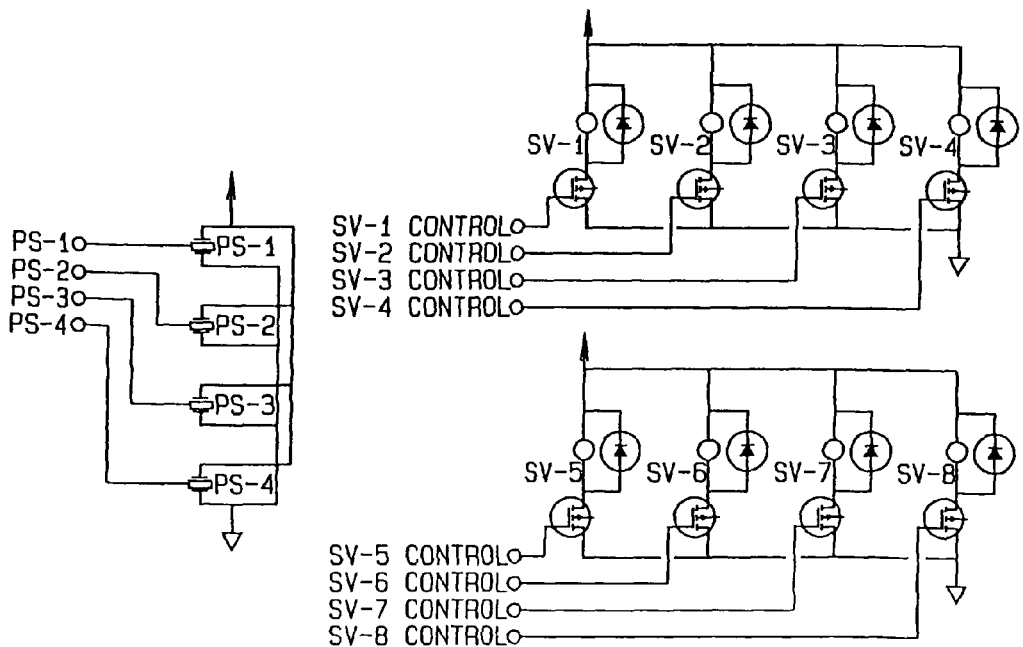
FIG. 15 is a further schematic of the circuitry used for the solenoid valves controlling the pneumatics for this compression garment.

The various FET transistors, and their association with the various valve solenoids, SV-1 through SV-8, can be seen in FIG. 15. In addition, the operations of the pressure sensors PS-1 through PS-4 can also be seen from this figure.

In the system operation, a microprocessor controller monitors the inputs from the keypad, the battery charger and monitoring circuits and the cell pressure sensors.

The serial data output from the microprocessor is used to send data to the LCD driver that displays operator information on the LCD. The display is activated in response to an operator input on the keypad, and any alarm condition or system failure. The LCD and keypad are backlit in response to a signal from the "light" button on the keypad. The backlighting remains on for a timed period and automatically turns off when no input from the keypad has been detected for a specified period.

Depending on pressure set point and the measured pressure from the pressure sensors, the electrically actuated solenoid valves are used to connect a cell to the pressure or vent manifold. Valve control signals from the microprocessor are connected to the gate input of a specified FET transistor. The FET provides low side switch control of the solenoid valves.

Prior to connecting a cell to the pressure manifold, the pump motor is turned on. The pump is controlled by a signal from the microprocessor that is connected to a FET transistor. The FET provides for low side switch control of the pump motor.

The system is designed to operate from a rechargeable battery. Separate circuitry provides for controlling the battery charge sequence and monitoring of the battery status. In the event of a low voltage condition, an alarm output is provided to the microprocessor. The system is capable of operating with a charged battery or with a 120v AC charger attached to the controller.

An audio alarm is provided to indicate an unrecoverable out of tolerance condition. The frequency and pulse length of the alarm tone are specific to individual alarm conditions, such as low battery voltage, over/under pressure, sensor failure, etc.

A further modification to the subject matter of this invention relates to the use of pads, as upon operation tables, on a hospital bed, or on a wheelchair, whether it be a pad that extends over the entire surface, or is provided under a select parts of the body, to function in the manner of this invention, for the purpose of relieving pressure point by alternating the amount of pressure applied to select cells of the pad, to reduce pressure at a pressure point, while increasing pressure in the pad cells in the adjacent areas. As a refresher, pressure ulcers formed due to the restriction of circulation to tissues that are located in areas which experience large, static pressure concentrations extending over long periods of time. The solution of the current pad/pump combination which supports the patient and supplies dynamic pressure radiance over the relevant physiological scale is design to relieve such ulcer generating areas. By dynamically changing the pressure profile under the patient, blood flow and lymph flow are stimulated on a continuous basis, preventing cell death, and hence pressure ulcers. The benefits to individuals, medical institutions, insurance companies, and the overall economy are innumerable.

Figure 16:
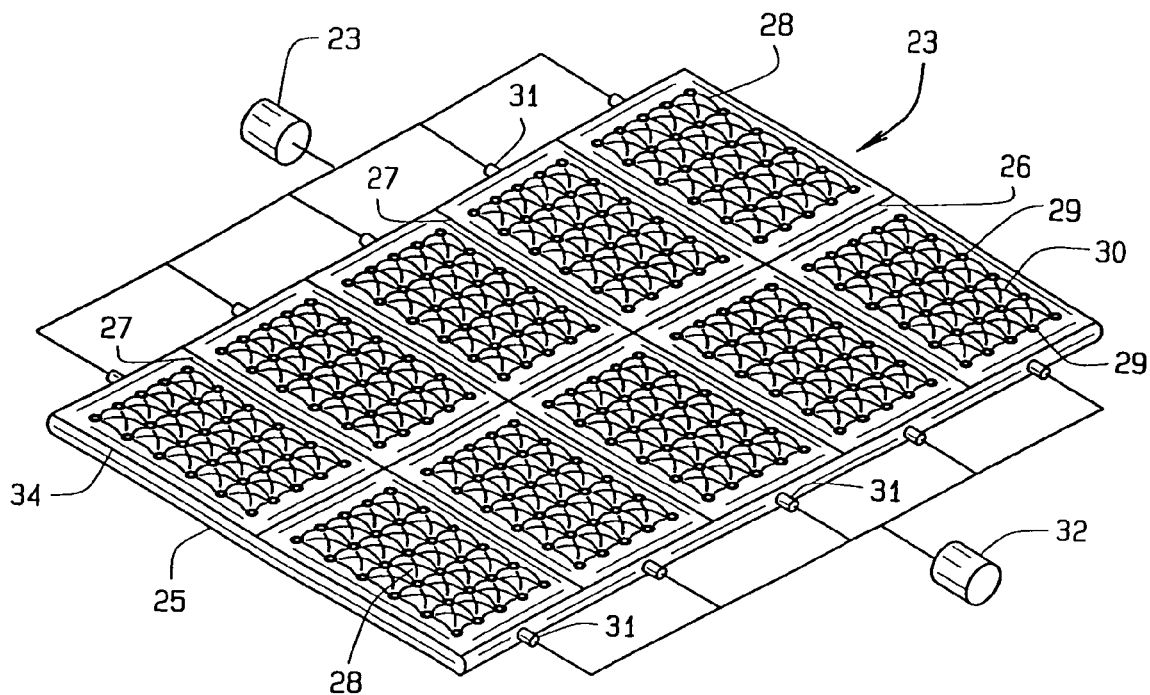
FIG. 16 is an isometric view of the segmented pneumatic pad where various areas may have regulated pressure in order to lessen the force upon a proximate body part, during usage.

FIG. 16 shows a further variation upon the pad of this invention, as noted at 23, and which pad is fabricated from a pair of laminated liners, such as at 24 and 25, in the manner similar to that as previously described for the garments herein, and has various seal lines, along its edges, in addition between various pad segments, as can be noted at 26 and 27, so that various segments 28 may be individually filled with air pressure, as desired, or other segments may be extracted of some air, so as to reduce their pressure, and lessen the amount of force that is applied by that segment against the body, as the pad is applied upon a hospital bed, the operating table, a bed at home, or at other locations. Each segment has the various grommets, as at 29, which allows for aeration provided therethrough, since they have apertures centrally located therein, and form various sub-segmented pockets, as at 30, which function in the manner as previously described for the garments explained in this application. Thus, not only are there select segments 28 for the segmented pad, but individual pockets 30 are formed therein, due to the presence of the sealed openings or grommets that are pressure sealed between the upper and lower liners 24 and 25, during formation of the pad of this invention. In addition, various valves, as at 31, are provided leading into each of the segments 28, these valves may be controlled by a control means, such as shown at 32, which incorporates a miniature pump, to provide for the addition of pressurized air into the various segments, depending upon the control of their valves, so as to increase the amount of pressurized air in select segments, but to reduce or vary the amount of pressurized air in other segments, for reasons as previously described herein. The pad of this invention functions not too unlike that of the types of compression garments as previously reviewed in this application, so that pressure can be varied, at select locations, to better allow for treatment of the infected patient requiring convalescence.

Figure 17:
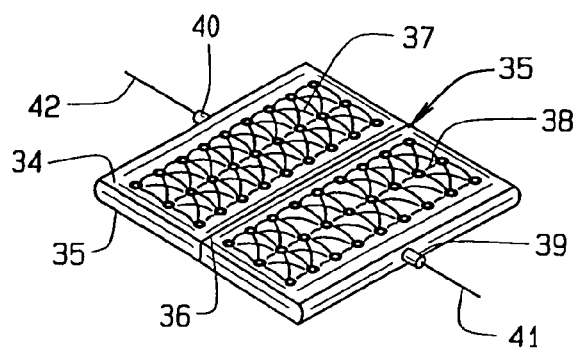
FIG. 17 discloses a miniature style of pad that may be used at isolated locations under the body, during usage.

FIG. 17 shows a similar type of pad 33, which is of smaller scale, and of the type that may rest upon a seat, or a wheelchair, but just under select parts of the patient body being treated, during usage. It likewise is formed of an upper and lower liner material, as at 34 and 35, which are performing as the upper and lower surfaces of the shown pad, but which are sealed together at their midpoint, as at 36, to form two segments 37 and 38 of the disclosed pad. Valves 39 and 40 are integrally connected for delivering pressurized air into the various pad segments, or for extracting air from therein, depending upon the regulated pressure required for the pad during its application. And, one or more controllers and pumps (not shown) similar to those previously described at 32, will communicate with the air lines 41 and 42 putting air into a particular pad segment, or for the controlled release of air therefrom, during usage of this smaller pad.

Figure 18:
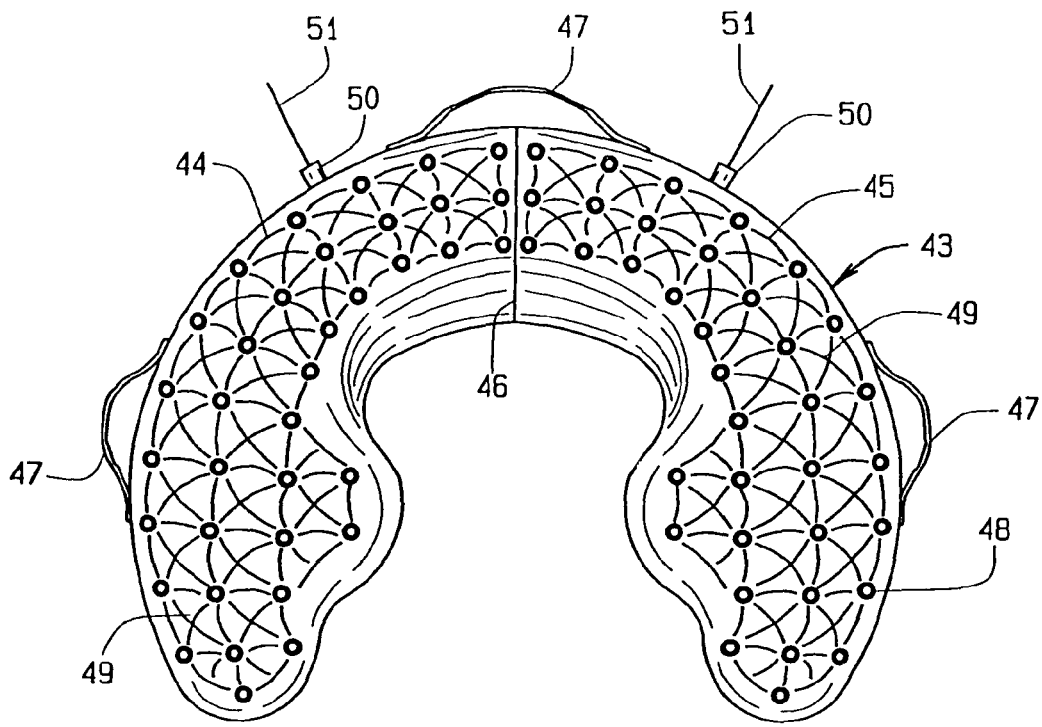
FIG. 18 shows another style of pad, which is further segmented, so as to regulate pressure exerted at various locations, as upon the buttocks, when the pad is set upon.

FIG. 18 shows how the pad may be formed into an arcuate cushion, as at 43, and which may be formed into two segments, as at 44 and 45, through the seal line 46 that fits between the two segments. In addition, handles, such as at 47 may be provided, to facilitate the manipulation of the pad, during its usage. And, each segment is formed having a series of spacedly arranged grommets, as at 48, between the upper and lower liners for the shown pad, in order to form the various air pockets 49, which function in the manner as previously described for the similar type of mats and garments. Various control valves 50 allow for the entrance or extraction of pressurized air into the various segments, through their connecting air lines 51, and which may further connect either to separate or the same controller and pump (not shown) similar to that at 32, as previously reviewed. This type of a mat can be used upon a chair, on the bed, the wheelchair, or the like, and which may be set upon, in order to regulate the amount of force applied to the contiguous surface of the body, or portions thereof, through the controlled operation of this particular style of arcuate mat, as can be seen. Obviously, this type of a mat, because of its configuration, could be segmented at various locations, around its perimeter, other than just having a singular seal line 46, as can be seen.

Figure 19:
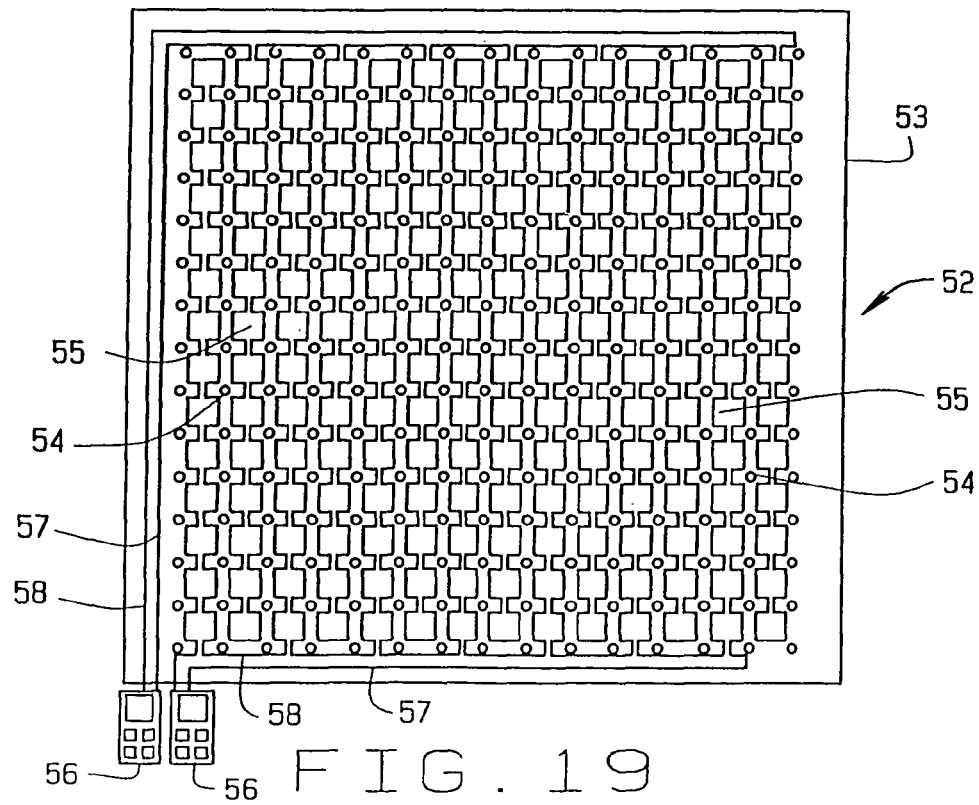
FIG. 19 shows a schematic of a pad, of this invention, the controllers for regulating the amount of air that is injected or extracted, from various segments of the shown pad.

Another style of pad, which could be to any dimension, can be seen in FIG. 19. This pad 52, likewise formed of upper and lower liner materials, and which are fastened together around their perimeter, as at 53, incorporate a series of grommets, as at 54, and functions to form small air pockets or pillows, as at 55, along the entire structure of the shown pad. Controllers that incorporate pressurized pumps, as noted at 56, are provided externally of the pad, but connect by air lines 57, are adding air into the various pockets, or can be used for evacuating air from the pockets, through their lines 58. In addition, valves may be provide at strategic locations, and which are regulated by the controllers, for either opening to allow the entrance of the pressurized air, from the miniature pumps, or for evacuating the same therefrom, through their respective air lines, to regulate the amount of pressure. This particular pad can likewise be segmented, although it is shown as a unitary pad in structure as noted in FIG. 19. Seal lines could be provided at various locations, in order to segregate the segments of the pad, to allow for the regulation and control of the pressurized air at select locations, where it may be required for either enhancing pressure around the location of a bed sore, or infection, or for reducing pressure at that segment of the pad, that contacts the infected area. This is an example as to how this type of a pad can be operated. The various controllers 56 have Velcro or other connecting means affixed to them, so that may be affixed in place, or removed, and repositioned, as desired and required.

Figure 20:
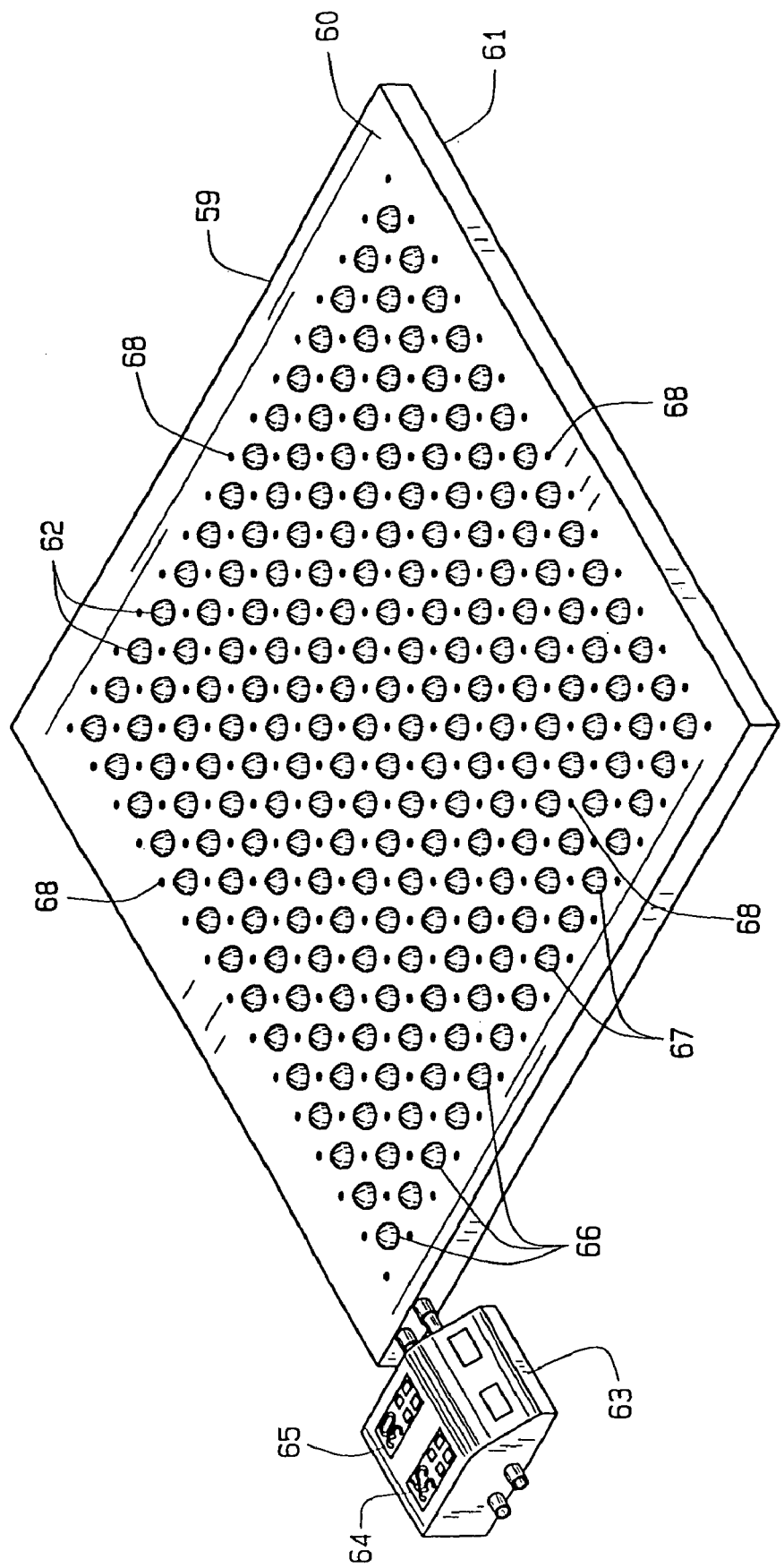
FIG. 20 shows a schematic of another pad, of this invention, with a controller for regulating the segments of the shown pad's application.

FIG. 20 is another pad, which can be of any size, it may be approximately one foot by one foot (1'×1') in dimension, or four feet by six feet (4'×6') to use for bed or operating table application. Essentially, the pad 59 is fabricated of an upper liner, as at 60, and a bottom liner 61, that are sealed together. The upper liner 60 is fabricated having a series of bubble like pillows, as at 62, which when the pad is inflated, through the use or application of pressurized air, the pillows will expand upwardly, to provide for that type of cushioning, selectively controlled, and for application of the shown pad or mat. A controller 63 which may have dual segments, as at 64 and 65, which incorporates the electronics for control of this device, includes a pair of miniaturized pumps, or at least one pump, that can be selectively directed to two portions of the pad, to provide for its controlled inflation, so as to maintain the amount of pressure that is built up in each pillow section 62, during its application. In this particular embodiment, each length of columns, or the odd number columns, such as columns 1,3,5, etc, as noted at 66, can be separately controlled by the controller segment 64, while the even numbered columns, such as 2,4,6,8,10, etc, as noted at 67, can be separately controlled by the controller segment 65, during its usage and application. But, it is just as likely that the air flow lines (not shown), deliver air to the selective columns of the pad, and could be segmented differently, so that, for example, the left half of the pad may be controlled by the air controller 64, while the right half of the pad may be controlled by the air controller segment 65. Or, quarter segments of the pad could be controlled separately, to provide the enhanced benefits as previously described for the variable pneumatic pad of this invention. Various valves can be applied for this purpose. In addition, there are a plurality of apertures, as at 68, provided through the pad, in proximity with each of the pillow sections 62, so that ventilation can be provided to the body part, resting upon the pad, during its usage, in the manner as previously explained with respect to the fabricated pads that are constructed as the earlier structured pads as defined in this application. These are examples of how the pad may be varied, in structure, but yet attain and achieve the related results of this invention.

It should be obvious to one skilled in the art, by now, that the various pads or mats of this invention, as described herein, and in particular in FIGS. 16 through 20 could also be applied to various parts or limbs of the body, and be wrapped therearound, to function in the manner of one of the garments as previously described in the application. Under said circumstances, any type of fastening means, such as Velcro strap, could be applied along the edges of the pads, to hold in place as a wrap when used and applied for this purpose.

Figure 22:
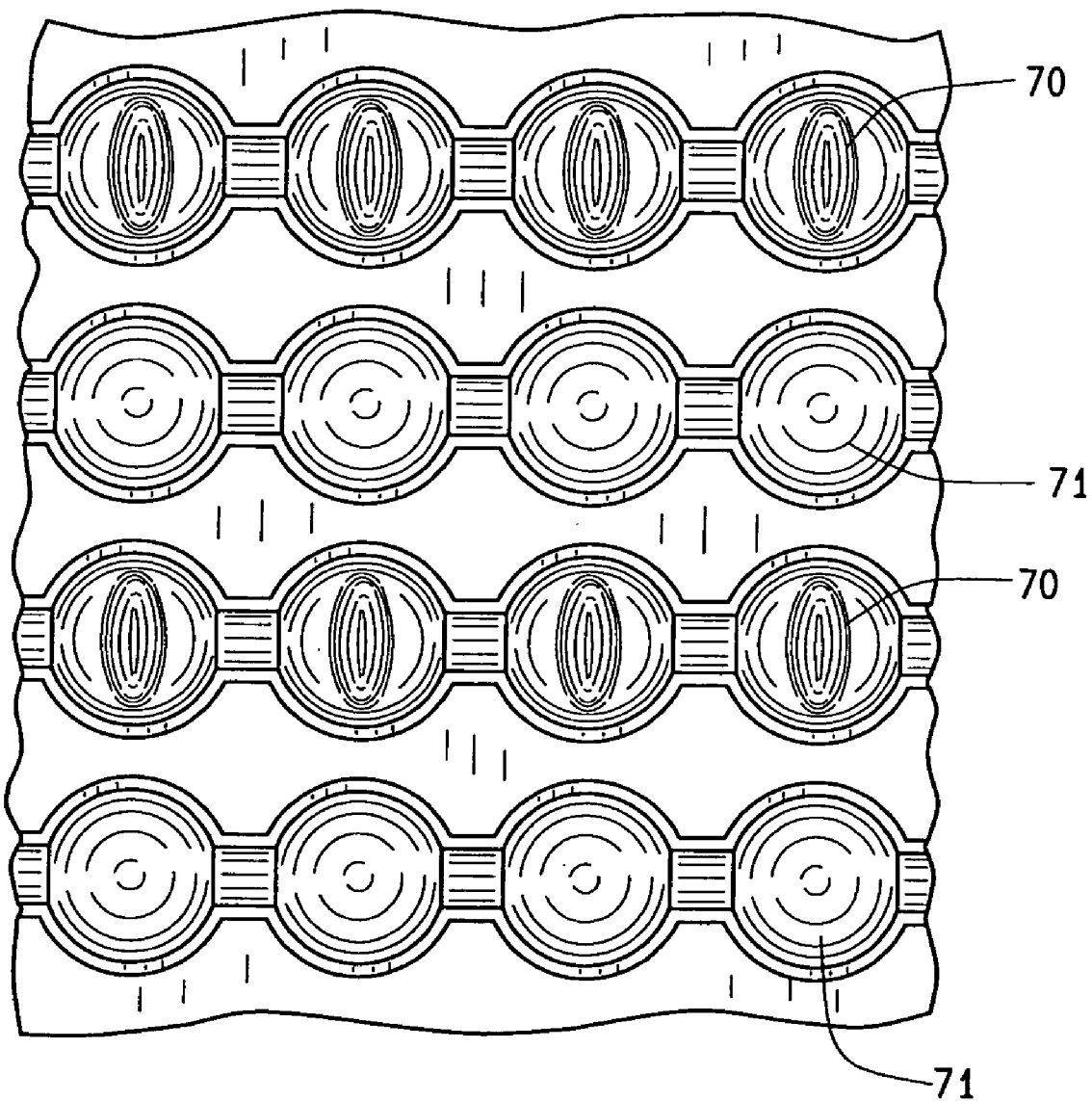
FIG. 22 show a further development modified for the pad of this invention wherein select air cells are inflated with the computer control pump for increasing pneumatic pressure on select areas upon the body, while reducing the pressure in adjacent air cells during usage of the pad appliance of this invention.

FIG. 22 shows a further modification in the structure of the pad of this invention. As disclosed, the air cells 70 in one row are in communication with each other, as can be noted, while the adjacent row of cells, as at 71, are unconnected with the cells 70. Each of the air cellules are inflated with the computer controlled pump and increased the pneumatic pressure where it contacts the cells to the skin, thereby forcing fluid from the afflicted area. To increase the effectiveness of this device, two zones are mapped out on the pad, a shown. Even number rows may comprise one zone, while the odd numbered rows may form another zone. Each zone consist of alternating rows of this small air cellules, either 70, or 71, and are configured to provided optimum therapy by that particular treatment. These two zones would be set to the same pressure but would inflate and deflate on different timed cycles. This keeps the fluids and nutrients flowing to the boney prominences where the pressure of the body weight can reduce or eliminate this fluid flow. Normally, this lack of nutrient-rich fluid flow leads to the pressure ulcers. But by alternating the increase of pressure, for example the even numbered roll of cellules, while decreasing the pressure in the adjacent rows, and alternating this pressure function over a sustained period of time, (as previously summarized) has been found to have a tendency to decrease the development of specific pressure points, upon the body, and thereby substantially reduces the occurrence of the formation of any pressure ulcers.

You should note that the cells, as at 71, of FIG. 22, are of a spherical design, but each of the cells within a row or interconnected together, so that air pressures is applied through that row, all of the cells become more inflated. But in addition, as can be noted at 70, where the cells are being deflated, the entire row becomes deflated together. But, it is to be noted that all of these air cells are of a spherical design, to enhance the application of pressure where needed, or relaxation of pressure, where required.

Figure 21A:
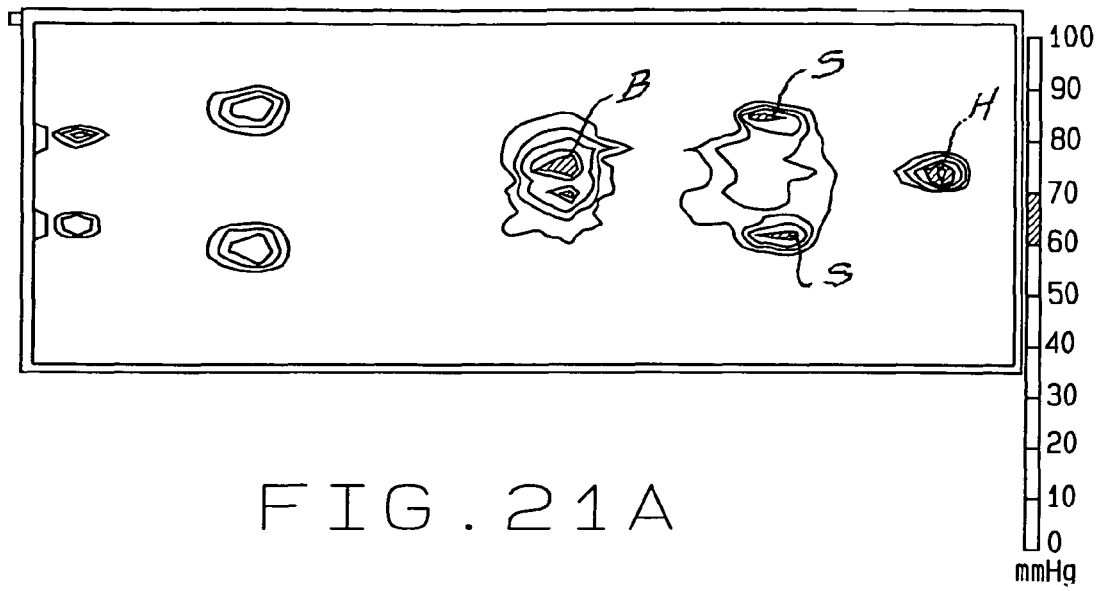
FIG. 21a shows the pressure exerted upon the body of a laying patient after lying at rest, as on a hospital bed, or an operating room table for some prolonged period of time, and showing the excessive pressure that builds up under select parts of the body during this period of time.
Figure 21B:
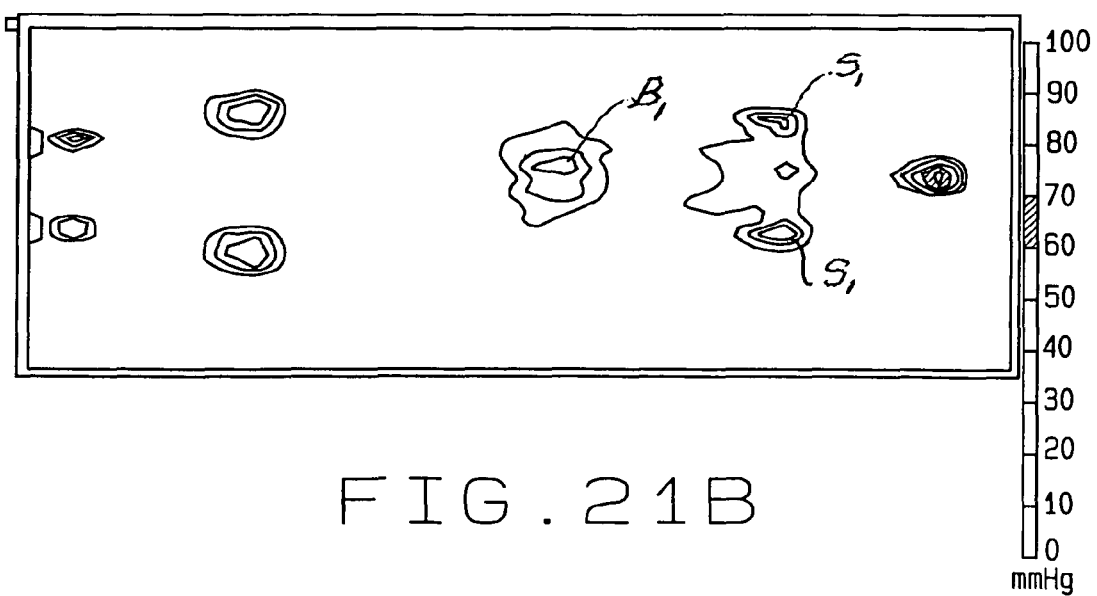
FIG. 21b shows how the pad of this invention as relieved the air pressure under the same select portions of the body, and has increased pressure in the surrounding area, so as to substantially reduce the pressure points that previously existed upon the same select parts of the body.

Furthermore, the entire pad, or any one of the pad of this invention, can be contained within a covering, such as in the nature of a pillow case, or the like, but which may be fabricated as the type of foam or related pad that is applied to an operating table currently. The pad will add further comfort to the application of the pressure from the pads of this invention, so as to relieve those pressure points as previously explained with respect to FIGS. 21*a* and 21*b*.

These appliances, as described herein, reduce edema wherever extra fluid may accumulate, i.e. pressure ulcers lymphatic insufficiency (lymphedema) areas of trauma (sprangs and surgical wounds) and venous insufficiency in the lower extremities (venous leg ulcers). Prevention of the generation of these types of danger areas upon the body is the major goal of this invention the prevention of pressure ulcers incurred by bed written or wheelchair bound patients, patients transported on gurneys in hospitals, and emergency rooms, and patients on operating room tables that are left for long periods of time.

Likewise, grommets, such as those previously described at 11, could be located between the various cells 70 and 71, as at the midpoint between four adjacent cells, in order to add some aeration to the pad during its usage and application.

Variations or modifications to the subject matter of this invention may occur to those skilled in the art upon reviewing the disclosure made herein. Such variations, if within the spirit of the desired results to be obtained from usage of this development, are intended to be encompassed within the scope of this invention as defined. The description of the preferred embodiment as set forth herein is done so for illustrative purposes only.

The invention claimed is:

1. A compression pad that is applied to various parts of the body of a patient to vary the amount of pressure upon the patient at select locations, said pad being formed having an upper layer and a lower layer of material, said upper and lower layers being of sufficient size and length to provide for location as a pad upon or under the patient being treated, said pad having sufficient length and width when applied upon or to a bed, a chair, operating table, or the like, said upper and lower layers of fabric material being sealed together around their margins, and intermediate thereof to provide various segments of internal pockets into which pressurized air may be injected during usage of the pad, a pump operatively associated with the upper and lower layers of the pad, and there being one valve member for each segment of an internal pocket, for injecting a pressurized air into each segment of the pad during usage, and each valve capable of being manipulated to provide for release of pressurized air from select segments of the pad, to provide for controlled pressure of the compression pad upon the patient during treatment;

there being a plurality of additional connections between the upper and lower layers of the fabric material within each segment of internal pocket to form a plurality of further segmented air pockets to provide a plurality of pressure points within each segment of an internal pocket for exertion by the compression pad upon that extremity of the body resting thereon, each of the plurality of additional connections forming the segmented air pockets within each segment of an internal pocket between the upper and lower layers of the pad being formed as sealed openings, and each of the further segmented air pockets in a segment being in communication with each other;

each segment of the pad having a valve provided therein, wherein air under pressure may be injected into each segment to inflate it to a particular and specified pressure, or the valve may provide for discharge of the pressurized air from select segments during usage;

means provided for determining the degree of pressurized air injected into each segment of the pad during usage, and said means comprising at least one controller;

each segmented air pocket having a pressure sensor operatively associated therewith to provide for a regulation of the pressure applied to select of said segmented air pockets, to detect the amount of pressure generated therein so as to vary the amount of pressure exerted upon the contiguous body parts of the patient and to provide for the increase or reduction in the amount of pressure within select air pockets in response thereto, and to reduce the amount of pressure in select air pockets to decrease the amount of pressure to select portions of the body where the pad is applied; and wherein each upper and lower layer is formed of fabric material, having a polymer coating applied thereto, and which is heat sealable to form the perimeter seal of each pad segment, and a plurality of segments being formed between the upper and lower layers of said pad.

2. The compression pad of claim 1 wherein the length and width of the compression pad is sized equivalent to the length and width of the bed or table upon which it is applied.

3. The compression pad of claim 1 wherein the length and width of the compression pad is sized for application to the seat of a chair to which the pad is applied.

4. The compression pad of claim 1 wherein the pad is arcuate in configuration.

5. The compression pad of claim 4 and including seals provided to separate the compression pad into various segments along its arcuate length.

6. The compression pad of claim 5 and including handles to facilitate the manipulation and location of the compression pad during its usage.

7. The compression pad of claim 1 wherein the pad may be wrapped around a portion of the user's body, and fastening means, operatively associated with select edges of the pad, to hold the pad in its wrapped position around the body portion.

8. The compression pad of claim 7 wherein said fastening means includes hook and pile type fasteners or straps for holding the pad in place.

9. The compression pad of claim 1 wherein said segmented air pockets are arranged in rows along the length of the formed pad, one row of segmented air pockets being inflated through operations of said pump, while the adjacent rows of segmented air pockets being deflated in pressure simultaneously, said controller also regulating the timed alternating sequence when one row of segmented air pockets are increased in pressure, while the adjacent rows of segmented air pockets are decreased in pressure through operations of the pump and valves.

10. The compression pad of claim 9 wherein each segmented air pocket within a row are in communication with each other so that as air pressure is elevated in one row, the entire row becomes inflated, and when air pressure is discharged from a row, the air in all of the communicating air pockets in that row are deflated.

11. The compression pad of claim 1 wherein the segmented air pockets are injected with air at approximately an upper psi, while the air in adjacent air pockets are deflated to approximately a lower psi, as the compression pad operates to alleviate pressure points upon the body of the patient during usage.

12. The compression pad of claim 11 wherein selected segmented air pockets are injected with air at approximately 0.5 to 3 psi, while the air in adjacent air pockets are deflated to approximately 0 to 0.1 psi, as the compression pad operates to alleviate pressure points upon the body of the patient during usage.

13. The compression pad of claim 12 wherein the air pockets are formed as cells.

14. A compression pad that is applied to various parts of the body of a patient to vary the amount of pressure upon the patient at select locations, said pad being formed having an upper layer and a lower layer of material, said upper and lower layers being of sufficient size and length to provide for location as a pad upon or under the patient being treated, said pad having sufficient length and width when applied upon or to a bed, a chair, operating table, or the like, said upper and lower layers of fabric material being sealed together around their margins, and intermediate thereof to provide various segments of internal pockets into which pressurized air may be injected during usage of the pad, a pump operatively associated with the upper and lower layers of the pad, and there being one valve member for each segment of an internal pocket, for injecting a pressurized air into each segment of the pad during usage, and each valve capable of being manipulated to provide for release of pressurized air from select segments of the pad, to provide for controlled pressure of the compression pad upon the patient during treatment;

there being a plurality of additional connections between the upper and lower layers of the fabric material within each segment of internal pocket to form a plurality of further segmented air pockets to provide a plurality of pressure points within each segment of an internal pocket for exertion by the compression pad upon that extremity of the body resting thereon; and each of the further segmented air pockets in a segment being in communication with each other;

each segment of the pad having a valve provided therein, wherein air under pressure may be injected into each segment to inflate it to a particular and specified pressure, or the valve may provide for discharge of the pressurized air from select segments during usage;

means provided for determining the degree of pressurized air injected into each segment of the pad during usage, and said means comprising at least one controller;

each segmented air pocket having a pressure sensor operatively associated therewith to provide for a regulation of the amount of pressure applied to select segmented air pockets, to detect the amount of pressure generated therein so as to vary the amount of pressure exerted upon the contiguous body parts of the patient, and to reduce the amount of pressure within select air pockets where pressure needs to be lessened to prevent damage to select body parts where the pad is applied; and wherein each upper and lower layer is formed, including polymer material, and which is heat sealable to form the perimeter seal of each pad segment, and a plurality of segments being formed between the upper and lower layers of said pad.

15. The compression pad of claim 14 wherein the pressure sensors are pressure transducers.

16. The compression pad of claim 14 wherein a sealed opening is provided with each segmented air pocket to provide for ventilation under the lower layer of the pad during its application while the patient rests thereon.

17. The compression pad of claim 16 wherein each sealed opening is formed by a grommet.

18. The compression pad of claim 17 wherein the sealed openings formed by grommets provide venting.

19. The compression pad of claim 17 wherein each connecting grommet has an aperture provided therethrough, to allow for ventilation under the lower layer of the pad during its application while the patient rests thereon.

20. A compression pad that is applied to various parts of the body of a patient to vary the amount of pressure upon the patient at select locations, said pad being formed of layers of material and being of sufficient size and length to provide for location as a pad upon or under a patient being treated, said pad having sufficient length and width when applied upon onto a bed, a chair, operating table, or the like, said layers of material being sealed together to accept air under pressure when inflated, said pad being further sealed to provide various segments of internal pockets into which the pressurized air may be selectively injected as during usage of the pad, a pump operatively associated with the pad, and there being a valve member for each segment of an internal pocket for injecting a pressurized air into each segment of the pad during usage, and each valve capable of being manipulated to provide for release of pressurized air from select segments of the pad to provide for controlled pressure of the compression pad upon the patient during treatment;

there being a plurality of additional connections between the various layers of the pad of each segment to form a plurality of further segmented air pockets to effect a plurality of pressure points within each segment of an internal pocket for exertion by compression upon that part of the body resting thereon, and providing for a release therefrom that part of the body which is subjected to an upper level of pressure that can cause body ulcers at that location;

means provided for determining the degree of pressurized air injected into each segment of the pad during usage, and said means comprising at least one controller;

each segmented air pocket having a pressure sensor operatively associated therewith to provide for a regulation of the pressure applied to select of said segmented air pockets, to detect the amount of pressure generated therein so as to vary the amount of pressure exerted upon the contiguous body parts of the patient and to provide for an increase or reduction in the amount of pressure within select air pockets in response thereto, and to reduce the amount of pressure in select air pockets to decrease the amount of pressure to select portions of the body where the pad is applied; and timing means operating within the controller to effect a timed elevation or release of pressure from select air pockets, and a decrease or increase alternately of pressurized air from the adjacent air pockets during usage of said pad.

21. A compression pad that is applied to various parts of the body of a patient to vary the amount of pressure upon the patient at select locations, said pad being formed of layers of material and being of sufficient size and length to provide for location as a pad under the patient being treated, said pad having sufficient length and width when applied onto a bed, a chair, operating table, or the like, said layers of material being sealed together to accept air under pressure when inflated, said pad being sealed to provide various segments of internal cells into which the pressurized air may be selectively injected as during usage of the pad, or air may be discharged, so as to lessen the amount of pressure applied by the pad within select segments, said cells of the segments of the pad being shaped of configuration, and arranged in longitudinal rows along the length of the pad;

Wherein the cells provided within a row of select segments of the compression pad are in communication with each other so that when air is injected into that segment, all of the cells are inflated, or when air is discharged from a segment of the pad, all of the cells in that row have reduced air pressure during usage of said pad;

means provided for determining the degree of pressurized air injected into each segment of the pad during usage, and said means comprising at least one controller;

each segment of the pad having a pressure sensor operatively associated therewith to provide for a regulation of the pressure applied to select air cells of the pad segments, to detect the amount of pressure generated therein so as to vary the amount of pressure exerted upon the contiguous body parts of the patient and to provide for an increase or reduction in the amount of pressure within select air cells in response thereto, and to reduce the amount of pressure in select air cells to decrease the amount of pressure to select portions of the body where the pad is applied, and timing means operating within the controller to effect a timed elevation or release of pressure from select segments of the pad and to decrease or increase alternately the pressurized air from the adjacent segments of the pad during usage of said pad; and there being one valve member for each segment of the said pad.

* * * * *